United States Patent
Weinberg

(10) Patent No.: US 11,426,394 B2
(45) Date of Patent: Aug. 30, 2022

(54) METHOD TO PREVENT AND TREAT MACULAR DEGENERATION BY CALCIUM CHANNEL BLOCKERS, ANGIOTENSIN CONVERTING ENZYME INHIBITORS, AND ANGIOTENSIN RECEPTOR BLOCKERS

(71) Applicant: Assa Weinberg, Los Angeles, CA (US)

(72) Inventor: Assa Weinberg, Los Angeles, CA (US)

(*) Notice: Subject to any disclaimer, the term of this patent is extended or adjusted under 35 U.S.C. 154(b) by 0 days.

(21) Appl. No.: 17/340,486

(22) Filed: Jun. 7, 2021

(65) Prior Publication Data

US 2021/0290607 A1 Sep. 23, 2021

Related U.S. Application Data

(63) Continuation of application No. PCT/US2019/065054, filed on Dec. 6, 2019.

(60) Provisional application No. 62/777,216, filed on Dec. 9, 2018, provisional application No. 62/777,214, filed on Dec. 9, 2018, provisional application No. 62/777,218, filed on Dec. 9, 2018.

(51) Int. Cl.

| | |
|---|---|
| *A61K 31/4422* | (2006.01) |
| *A61P 27/02* | (2006.01) |
| *A61K 31/04* | (2006.01) |
| *A61K 31/138* | (2006.01) |
| *A61K 31/165* | (2006.01) |
| *A61K 31/166* | (2006.01) |
| *A61K 31/167* | (2006.01) |
| *A61K 31/18* | (2006.01) |
| *A61K 31/216* | (2006.01) |
| *A61K 31/277* | (2006.01) |
| *A61K 31/345* | (2006.01) |
| *A61K 31/401* | (2006.01) |
| *A61K 31/403* | (2006.01) |
| *A61K 31/404* | (2006.01) |
| *A61K 31/41* | (2006.01) |
| *A61K 31/4178* | (2006.01) |
| *A61K 31/4184* | (2006.01) |
| *A61K 31/4245* | (2006.01) |
| *A61K 31/4439* | (2006.01) |
| *A61K 31/472* | (2006.01) |
| *A61K 31/50* | (2006.01) |
| *A61K 31/517* | (2006.01) |
| *A61K 31/549* | (2006.01) |
| *A61K 31/55* | (2006.01) |
| *A61K 31/554* | (2006.01) |
| *A61K 31/675* | (2006.01) |

(52) U.S. Cl.
CPC .......... *A61K 31/4422* (2013.01); *A61K 31/04* (2013.01); *A61K 31/138* (2013.01); *A61K 31/165* (2013.01); *A61K 31/166* (2013.01); *A61K 31/167* (2013.01); *A61K 31/18* (2013.01); *A61K 31/216* (2013.01); *A61K 31/277* (2013.01); *A61K 31/345* (2013.01); *A61K 31/401* (2013.01); *A61K 31/403* (2013.01); *A61K 31/404* (2013.01); *A61K 31/41* (2013.01); *A61K 31/4178* (2013.01); *A61K 31/4184* (2013.01); *A61K 31/4245* (2013.01); *A61K 31/4439* (2013.01); *A61K 31/472* (2013.01); *A61K 31/50* (2013.01); *A61K 31/517* (2013.01); *A61K 31/549* (2013.01); *A61K 31/55* (2013.01); *A61K 31/554* (2013.01); *A61K 31/675* (2013.01); *A61P 27/02* (2018.01)

(58) Field of Classification Search
None
See application file for complete search history.

(56) References Cited

U.S. PATENT DOCUMENTS

| | | | |
|---|---|---|---|
| 4,981,871 A | 1/1991 | Abelson | |
| 5,278,172 A | 1/1994 | Hennessey | |
| 5,431,907 A | 7/1995 | Abelson et al. | |
| 5,435,998 A | 7/1995 | Abelson | |
| 5,525,601 A | 6/1996 | Belmonte-Martinez et al. | |
| 5,612,382 A | 3/1997 | Fike | |
| 5,827,862 A | 10/1998 | Yamamura | |
| 6,001,368 A | 12/1999 | Jenks | |
| 6,093,417 A | 7/2000 | Petrus | |
| 6,221,915 B1 | 4/2001 | McCleane | |
| 6,716,835 B1 * | 4/2004 | Picaud | A61P 27/02 514/211.07 |

(Continued)

FOREIGN PATENT DOCUMENTS

| | | |
|---|---|---|
| AT | 407482 B | 3/2001 |
| DE | 102016207337 A1 | 11/2017 |

(Continued)

OTHER PUBLICATIONS

Laws, H. Canad. Med. Assn. J. 1964, vol. 91, pp. 325-330.*
Leung, E. Exp. Rev Clin Pharmacol. 2013 vol. 6, pp. 565-579.*
Age-Related Eye Disease Study 2 Research Group, "Lutein + zeaxanthin and omega-3 fatty acids for age-related macular degeneration: the Age-Related Eye Disease Study 2 (AREDS2) randomized clinical trial", JAMA, 2013; vol. 309, No. 19, pp. 2005-2015.

(Continued)

*Primary Examiner* — Heidi Reese
(74) *Attorney, Agent, or Firm* — Knobbe, Martens, Olson & Bear, LLP

(57) ABSTRACT

A method is provided to prevent and to treat Macular Degeneration by using Calcium Channel Blockers, Angiotensin-Converting Enzyme (ACE) Inhibitors, or Angiotensin Receptor Blockers (ARB), and more particularly, to a method to prevent and treat Macular Degeneration by using Calcium Channel Blockers, Angiotensin-Converting Enzyme Inhibitors, or Angiotensin Receptor Blockers that are not taken orally, but administered by ophthalmic preparation directly onto or into the eye where Macular Degeneration is formed, to increase the capillary network and blood supply to the retinal macula.

12 Claims, No Drawings

(56) References Cited

U.S. PATENT DOCUMENTS

| | | |
|---|---|---|
| 6,747,008 B1 | 6/2004 | Rodgers et al. |
| 7,094,431 B2 | 8/2006 | Peshoff |
| 7,767,710 B2 | 8/2010 | Waddell |
| 7,871,647 B1 | 1/2011 | Paradise |
| 8,211,947 B2 | 7/2012 | Sosa |
| 8,765,678 B2 | 7/2014 | Weinstein et al. |
| 2002/0099003 A1 | 7/2002 | Wilson et al. |
| 2005/0176782 A1 | 8/2005 | Easterling |
| 2005/0222127 A1 | 10/2005 | Sharif |
| 2006/0079467 A1 | 4/2006 | Jia et al. |
| 2006/0269579 A1 | 11/2006 | Waddell |
| 2006/0292213 A1 | 12/2006 | Gerber et al. |
| 2007/0160648 A1 | 7/2007 | Ashton et al. |
| 2007/0196495 A1* | 8/2007 | Soltero ............. A61K 9/2063 424/488 |
| 2009/0018151 A1 | 1/2009 | Fink |
| 2011/0081323 A1 | 4/2011 | Kleinsek et al. |
| 2011/0196035 A1 | 8/2011 | Kolomytkin et al. |
| 2011/0212157 A1 | 9/2011 | Edelson et al. |
| 2012/0238498 A1 | 9/2012 | Endo |
| 2013/0029989 A1 | 1/2013 | Coderre et al. |
| 2013/0053393 A1 | 2/2013 | Frangakis et al. |
| 2013/0209545 A1 | 8/2013 | Twidwell et al. |
| 2013/0302444 A1 | 11/2013 | Miller et al. |
| 2013/0303566 A1 | 11/2013 | Hill |
| 2014/0357645 A1 | 12/2014 | Kopacki et al. |
| 2016/0243080 A1 | 8/2016 | Abadir et al. |
| 2017/0020913 A1 | 1/2017 | Pilotto et al. |
| 2017/0348277 A1 | 12/2017 | Ruiz |
| 2018/0344714 A1 | 12/2018 | Wasan |
| 2019/0321372 A1 | 10/2019 | Wittel et al. |
| 2021/0069102 A1 | 3/2021 | Weinberg |
| 2021/0069108 A1 | 3/2021 | Weinberg |
| 2021/0290607 A1 | 9/2021 | Weinberg |

FOREIGN PATENT DOCUMENTS

| | | |
|---|---|---|
| WO | WO 2008/016358 A1 | 2/2008 |
| WO | WO 2009/042854 A1 | 4/2009 |
| WO | WO 2019/226542 A1 | 11/2019 |
| WO | WO 2019/226548 A1 | 11/2019 |
| WO | WO 2020/118254 A1 | 6/2020 |
| WO | WO 2021/076218 A1 | 4/2021 |

OTHER PUBLICATIONS

Age-Related Eye Disease Study Research Group, "A randomized, placebo-controlled, clinical trial of high-dose supplementation with vitamins C and E, beta carotene, and zinc for age-related macular degeneration and vision loss", Arch Ophthalmol, 2001, vol. 119, pp. 1417-1436.

Amory, John K. et al., "The effect of 5alpha-reductase inhibition with dutasteride and finasteride on semen parameters and serum hormones in healthy men", J Clin Endocrinol Metab, 2007; 92:1659-1665.

Arlinger S. Negative consequences of uncorrected hearing loss—a review. Int J Audiol 2003; 42 Suppl 2:2S17.

Arnold LM, et al. AAPT Diagnostic Criteria for Fibromyalgia. J Pain 2019; 20:611.

Bazzichi L, et al. Cytokine patterns in fibromyalgia and their correlation with clinical manifestations. Clin Exp Rheumatol 2007; 25:225.

Blagojevic M., et al.Risk factors for onset of osteoarthritis of the knee in older adults: a systematic review and meta-analysis. Osteoarthritis Cartilage 2010; 18:24.

Buskila D, et al. Biology and therapy of fibromyalgia. Genetic aspects of fibromyalgia syndrome. Arthritis Res Ther 2006.

Christen W., et al. Smoking cessation and risk of age-related cataract in men, JAMA 2000; 284:713.

De Tommaso M,et al. Clinical features of headache patients with fibromyalgia comorbidity. J Headache Pain 2011 ;12:629.

Dietrich T, et al. Age-dependent associations between chronic periodontitis/edentulism and risk of coronary heart disease. Circulation 2008; 117:1668.

Dubois et al., "N-acetylcarnosine (NAC) drops for age-related cataract", Cochrane Database of Systematic Reviews 2017, Issue 2. Art. No.: CD009493, (Year: 2017).

Ebner H, et al. Allergic contact dermatitis from minoxidil. Contact Dermatitis 1995; 32:316.

El Maghraoui A, et al. Bone turnover and hormonal perturbations in patients with fibromyalgia. Clin Exp Rheumatol 2006; 24:428.

Elkana O, et al. Does the cognitive index of the symptom severity scale evaluate cognition? Data from subjective and objective cognitive measures in fibromyalgia. Clin Exp Rheumatol 2019; 37 Suppl 116:51.

Ettle et al., "Inhibition of experimental diabetic cataract by topical administration of RS-verapamil hydrochloride", Br. J. Opthalmol., 2004, vol. 88, pp. 44-47 (Year: 2004).

Farghaly et al. "Ameliorative effect of acetly-L-carnitine and/or nifedipine against selenite-induced cataractogenesis in young albino rats", European Journal of Pharmacology, 2014, vol. 729, pp. 1-9 (Year: 2014).

Gold E., et al., Longitudinal analysis of the association between vasomotor symptoms and race/ethnicity across the menopausal transition: study of women's health across the nation American journal of public health. Jul. 2006;96(7):1226-35.

Godfraind T. Discovery and development of calcium channel blockers. Frontiers in pharmacology. May 29, 2017;8:286.

Gregson CL, et al. High Bone Mass is associated with bone-forming features of osteoarthritis in non-weight bearing joints independent of body mass index. Bone 2017; 97:306.

Grunwald JE, et al. Reduced foveolar choroidal blood flow in eyes with increasing AMD severity. Invest Ophthalmol Vis Sci 2005; 46:1033.

Haldeman-Englert, "Vascular Endothelial Growth Factor", University of Rochester Medica Center Health Encyclopedia [online], 2020 [retrieved on Oct. 13, 2020]. Retrieved from <URL:https://www.urmc.rochester.edu/encyclopediac/ontent.aspx?ContentTypeID=167&ContentID=v gf> p. 1.

Harris R, et al. Decreased central mu-opioid receptor availability in fibromyalgia. J Neurosci 2007; 27:10000.

Harlow SD, et al. Executive summary of the Stages of Reproductive Aging Workshop+ 10: addressing the unfinished agenda of staging 1;97(4):1159-68.

Hauser W, et al. Efficacy of different types of aerobic exercise in fibromyalgia syndrome: a systematic review and meta-analysis of randomised controlled trials. Arthritis Res Ther 2010;12:R79.

Hirsso P, et al. Health-related quality of life and physical well-being among a 63-year-old cohort of women with androgenetic alopecia; a Finnish population-based study. Health Qual Life Outcomes 2005; 3:49.

Houston, "The Role of Magnesium in Hypertension and Cardiovascular Disease", The Journal of Clinical Hypertension, vol. 13, pp. 843-847.

Johnson MC, et al. Biochemical study of the relationship of extracellular glucan to adherence and cariogenicity in *Streptococcus* mutans and an extracellular polysaccharide mutant. J Bacteriol 1977; 129:351.

Kametaka et al., "Effect if Nifedipine on Severe Experimental Cataract in Diabetic Rats", Journal of Pharmacological Scienecs, 2008, vol. 106, No. 4, pp. 651-658 (Year: 2008).

Khan JC, et al. Smoking and age related macular degeneration: the number of pack years of cigarette smoking is a major determinant of risk for both geographic atrophy and choroidal neovascularisation. Br J Ophthalmol 2006; 90:75.

Klein, BE, et al. Long term use of aspirin and age related macular degeneration. 2012, JAMA DES; 308 (23) 2469-78.

Klein BE, et al. Risk of incident age-related eye diseases in people with an affected sibling: The Beaver Dam Eye Study. Am J Epidemiol 2001; 154:207.

Klein R, et al. Relation of smoking to the incidence of age-related maculopathy. The Beaver Dam Eye Study. Am J Epidemiol 1998; 147:103.

(56) References Cited

OTHER PUBLICATIONS

Kong L, et al. Association between smoking and risk of knee osteoarthritis: A systematic review and meta-analysis. Osteoarthritis Cartilage 2017; 25:809.
Krebs EE, et al. Effect of Opioid vs Nonopioid Medications on Pain-Related Function in Patients With Chronic Back Pain or Hip or Knee Osteoarthritis Pain: The SPACE Randomized Clinical Trial. JAMA 2018; 319:872.
Kuchinad A, et al. Accelerated brain gray matter loss in fibromyalgia patients: premature aging of the brain? J Neurosci 2007; 27:4004.
Lane NE, et al. OARSI-FDA initiative: defining the disease state of osteoarthritis. Osteoarthritis Cartilage 2011; 19:478.
Laws, Wyatt H., "Peripheral Vasodilators in the Treatment of Macular Degenerative Changes in the Eye", Canad. Med. Assn. J., 1964, vol. 91, pp. 325-330.
Lerma C, et al. Nocturnal heart rate variability parameters as potential fibromyalgia biomarker: correlation with symptoms severity. Arthritis Res Ther 2011; 13:R185.
Li M, et al. Minoxidil-induced hair growth is mediated by adenosine in cultured dermal papilla cells: possible involvement of sulfonylurea receptor 2B as a target of minoxidil. J Invest Dermatol 2001; 117:1594.
Limer KL, et al.Exploring the genetic susceptibility of chronic widespread pain: the tender points in genetic association studies. Rheumatology (Oxford) 2008;47:572.
Lin FR, et al. Hearing loss and incident dementia. Arch Neurol 2011; 68:214.
Lindblad BE. et al., Smoking cessation andthe risk of cataract: a prospective cohort study of cataract extraction among men. JAMA Ophthalmol 2014; 132:253.
Lutz J, et al. White and gray matter abnormalities in the brain of patients with fibromyalgia: a diffusion-tensor and volumetric imaging study. Arthritis Rheum 2008; 58:3960.
Maekawa K. et al. Function of beta-adrenergic receptors on mononuclear cells in female patients with fibromyalgia. J Rheumatol 2003; 30:364.
Manson JE, et al., Menopausal hormone therapy and health outcomes during the intervention and extended poststopping phases of the Women's Health Initiative randomized trials, JAMA 2013; 310:1353.
Mares J. et al. Healthy lifestyles related to subsequent prevalence of age related macular degeneration. Arch Ophthalmol 2011; 129:470.
Mares J., et al. Healthy diets and the subsequent prevalence of nuclear cataract in women. Arch; Moeller SM, Voland R, Tinker L, et al., Associations between age-related nuclear cataract and lutein and zeaxanthin in the diet and serum in the Carotenoids in the Age-Related EyeDisease Study, an Ancillary Study of the Women's Health Initiative.Arch Ophthalmol 2008; 126:354.
McBeth J. et al., Predictors of new-onset widespread pain in older adults: results from a population-based prospective cohort study in the UK. Arthritis Rheumatol 2014: 66:757.
McLean S. et al. Momentary relationship between cortisol secretion and symptoms in patients with ftbromyalgia. Atthritis Rheum 2005; 52:3660.
Mitchell CM.et al., Efficacy of vaginal estradiol or vaginal moisturizer vs placebo for treating postmenopausal vulvovaginal symptoms: a randomized clinical trial. JAMA internal medicine. May 1, 2018;178(5):681-90.
Moisio K.et al., Varus-valgus alignment: reduced risk of subsequent cartilage loss in the less loaded compartment. Arthritis Rheum 2011; 63:1002.
Mondelli et al, Quality of life in elderly adults before and after hearing aid fitting. Braz J Otorhinolaryngol 2012; 78:49.
Myung P. et al. Dissecting the bulge in hair regeneration. J Clin Invest 2012; 122:448.
Murphy L., et al., Lifetime risk of symptomatic knee osteoarthritis. Arthritis Rheum 2008; 59:1207.
Nair, J., et al., "Eye", 2009, vol. 23, pp. 989-990 (Year: 2009).

Nash SD. et al. The prevalence of hearing impairment and associated risk factors: the Beaver Dam Offspring Study. Arch Otolaryngol Head Neck Surg 2011; 137:432.
Nishikai M. et al., Autoantibodies to a 68/48 kDa protein in chroruc fatigue syndrome and primary fibromyalgia: a possible marker for hypersomnia and cognitive disorders. Rheumatology (Oxford) 2001; 40:806.
Owen CG. et al. The estimated prevalence and incidence of late stage age related macular degeneration in the UK. Br J Ophthalmol 2012; 96:752.
Rahimi-Ardabili B. et al. Finasteride induced depression: a prospective study. BMC Clin Pharmacol 2006; 6:7.
Randolph Jr JF. et al.,The value of follicle-stimulating hormone concentration and clinical findings as markers of the late menopausal transition. The Journal of Clinical Endocrinology & Metabolism. Aug. 1, 2006;91(8):3034-40.
Randolph Jr JF. et al., The relationship of longitudinal change in reproductive hormones and vasomotor symptoms during the menopausal transition. The Journal of Clinical Endocrinology & Metabolism. Nov. 1, 2005;90(11):6106-12.
Rein DB. et al., Forecasting age-related macular degeneration through the year 2050: the potential impact of new treatments. Arch Ophthalmol 2009; 127:533.
Rizzi M. et al. Cyclic alternating pattern: a new marker of sleep alteration in patients with fibromyalgia? J Rbeumatol 2004; 31:1193.
Russell IJ. et al. Elevated cerebrospinal fluid levels of substance P in patients with the fibromyalgia syndrome. Arthritis Rheum 1994; 37:1593.
Santen RJ. et al., A. Postmenopausal hormone therapy: an Endocrine Society scientific statement. The Journal of Clinical Endocrinology & Metabolism. Jul. 1, 2010;95(7_supplement_1):s1-66.
Sawaya ME. Purification of androgen receptors in human sebocytes and hair. J Invest Dermatol 1992; 98:92S.
Seddon JM. et al. Progression of age-related macular degeneration: prospective assessment of C-reactive protein, interleukin 6, and other cardiovascular biomarkers. Arch Ophthalmol 2005; 123:774.
Sica, "Minoxidil: An Underused Vasodilator for Resistant or Severe Hypertension", The Journal of Clinical Hypertension, 6: 283-278. doi:10.1111/j. 1524-6175.2004.03585.x, Abstract.
Srikuea R, et al. Association of fibromyalgia with altered skeletal muscle characteristics which may contribute to postexertional fatigue in postmenopausal women. Arthritis Rheum 2013; 65:519.
Stocche et al., Rev. Bras. Anestesiol., 2002, vol. 52, No. 4, pp. 426-433 (ABSTRACT attached) (Year: 2002).
Stone EM, et al. Missense variations in the fibulin 5 gene and age-related macular degeneration. N Engl J Med 2004; 351 :346.
Stuenkel CA. et al.,Treatment of symptoms of the menopause: an endocrine society clinical practice guideline. The Journal of Clinical Endocrinology & Metabolism. Nov. 1, 2015;100(11):3975-4011.
Su LH. et al., Association of androgenetic alopecia with mortality from diabetes mellitus and heart disease. JAMA Dermatol 2013; 149:601.
Tepper PG et al.,Characterizing the trajectories of vasomotor symptoms across the menopausal transition. Menopause (New York, NY). Oct. 2016;23(10):1067.
Thompson IM et al. The influence of finasteride on the development of prostate cancer. N Engl J Med 2003; 349:215.
Tonetti MS, et al. Treatment of periodontitis and endothelial function. N Engl J Med 2007; 356:911.
Uceyler N. et al. Systematic review with meta-analysis: cytokines in fibromyalgia syndrome. BMC Musculoskelet Disord 2011; 12:245.
Uceyler N.et al., Small fibre pathology in patients with fibromyalgia syndrome. Brain 2013; 136:1857.
Vina ER. et al. Epidemiology of osteoarthritis: literature update. Curr Opin Rheumatol 2018; 30:160.
Vincent A, Lahr BD, Wolfe F, et al. Prevalence of fibromyalgia: a population-based study in Olmsted County, Minnesota, utilizing the Rochester Epidemiology Project. Arthritis Care Res (Hoboken) 2013; 65:786.
Walitt B. et al., Characterizing "fibrofog": Subjective appraisal, objective performance, and task-related brain activity during a working memory task. Neuroimage Clin 2016; 11: 173.

(56) References Cited

OTHER PUBLICATIONS

Walitt B. et al., The longitudinal outcome of fibromyalgia: a study of 1555 patients. J Rheumatol 2011 ; 38:2238.

Walitt B. et al., The Prevalence and Characteristics of Fibromyalgia in the 2012 National Health Interview Survey. PLoS One 2015; 10:e0138024.

Wattamwar K. et al., Increases in the Rate of Age-Related Hearing Loss in the Older Old. JAMA Otolaryngol Head Neck Surg 2017; 143:41.

Weih LM. et al., Age-specific causes of bilateral visual impairment. Arch Ophthalmol 2000; 118:264.

West SK. et al., Sunlight exposureand risk of lens opacities in a population-based study: the Salisbury Eye Evaluation project. JAMA 1998; 280:714.

White KP. et al., Comparing self reported function and work disability in 100 community cases of fibromyalgia syndrome versus controls in London, Ontario: the London Fibromyalgia Epidemiology Study. Arthritis Rheum 1999; 42:76.

Williams, B., Drug discovery in renin-angiotensin system intervention: past and future. Therapeutic Advances in Cardiovascular Disease, Jun. 2016; 10(3): 118-25.

Wolfe F.et al., Health status and disease severity in fibromyalgia: results of a six-center longitudinal study, Arthritis & Rheumatism, vol. 40, 1997, 1571-1579.

Worzala K. et al., Postmenopausal estrogen use, type of menopause, and lens opacities: the Framingham studies. Arch Intern Med 2001; 161:1448.

Yang Z., et al. Toll-like receptor 3 and geographic atrophy in age-related macular degeneration. N Engl J Med 2008;359:1456.

Yeung WK. et al., Comparison of sleep structure and psychometric profiles in patients with fibromyalgia, osteoarthritis and healthy controls. Sleep Res 2018; 27:290.

Zhang W., et al. OARSI recommendations for the management of hip and knee osteoarthritis: part III: Changes in evidence following systematic cumulative update of research published through Jan. 2009. Osteoarthritis Cartilage 2010; 18:476.

* cited by examiner

METHOD TO PREVENT AND TREAT MACULAR DEGENERATION BY CALCIUM CHANNEL BLOCKERS, ANGIOTENSIN CONVERTING ENZYME INHIBITORS, AND ANGIOTENSIN RECEPTOR BLOCKERS

INCORPORATION BY REFERENCE TO RELATED APPLICATION

Any and all priority claims identified in the Application Data Sheet, or any correction thereto, are hereby incorporated by reference under 37 CFR 1.57. This application is a continuation of and claims benefit of Application No. PCT/US2019/065054, filed Dec. 6, 2019, which claims the benefit of U.S. Provisional Application No. 62/777,214, filed December 9, 2018, U.S. Provisional Application No. 62/777,216, filed Dec. 9, 2018, U.S. Provisional Application No. 62/777,218, filed Dec. 9, 2018. The aforementioned application is incorporated by reference herein in its entirety, and is hereby expressly made a part of this specification.

FIELD OF THE INVENTION

A method is provided to prevent and to treat Macular Degeneration by using Calcium Channel Blockers, Angiotensin-Converting Enzyme (ACE) Inhibitors, or Angiotensin Receptor Blockers (ARB), and more particularly, to a method to prevent and treat Macular Degeneration by using Calcium Channel Blockers, Angiotensin-Converting Enzyme Inhibitors, or Angiotensin Receptor Blockers that are not taken orally, but administered by ophthalmic preparation directly onto or into the eye where Macular Degeneration is formed, to increase the capillary network and blood supply to the retinal macula.

BACKGROUND OF THE INVENTION

Visual impairment is a major health hazard for older adults. Normal vision is one of the most significant ingredients of life quality. Impaired vision interferes with the performance of the basic activities of daily living of people of any age. Vision impairment in elder persons increases the incidence of fall, and is one of the main causes for hip fracture, surgical hip repair, and total hip replacement in the US.

The macula is the central portion of the retina. The macula is responsible for the central vision's functions of the eye. Central vision is essential for tasks such as reading, watching television, navigating, or car driving.

Age-related macular degeneration affects the central portion of the retina and leads to central vision loss. Macular degeneration is the world's leading cause of blindness in the elderly. Clinically, macular degeneration is classified as dry (or atrophic), or wet (exudative). The dry type of the disease is pathologically characterized by 4 successive steps that lead to vision loss. First, localized or widespread areas of atrophy are observed in the pigment epithelial membrane. That area carries the photosensitive receptor cells of the retina. The atrophy is followed by pigmented epithelial and photoreceptors cells detachment from the retinal membranes. The detachment is followed by photoreceptors cell clumping. Finally, a thinning of the central retina membrane is observed, indicating cell death and loss of vision.

The advanced form of dry macular degeneration, also referred to as the geographic atrophy, is characterized by atrophy and cell death in territories outside the central portion of the retina. This dry advanced form is responsible for 10 percent of the legal blindness of the elderly. Dry macular degeneration is associated with widespread deposits of fatty extracellular bodies in the central region of the retina. These materials are called drusen. Drusen and Gingival Recession are the most common age related human biological processes worldwide. Some drusen appears in the retina of all people above age of 50. Drusen can be small or large, hard or soft, crystal clear or calcific. It is the large and soft drusen deposits that are associated with blindness.

The wet form of macular degeneration presents as acute loss of central vision by sub retinal hemorrhage. It is characterized by invasion and occupation of the sub retinal space by abnormally leaking capillaries. The capillary leaks cause edema, fluid collection, and swelling in the sub retinal space. Multiple hemorrhages appear under the Bruch membrane, which is the space under the retina basal membrane. This leads to rapid cell death of the specialized epithelial pigmented cells. These are the photosensitive receptors containing cells responsible for vision. This form is also called choroidal neo vascularization.

The dry forum of macular degeneration can convert to the wet one. 1 to 4 percent of patients with the dry form of macular degeneration are observed to progress to the wet form in one year. This number increases to 18 percent at the end of 3 years. The dry form of macular degeneration is a slow progressive process that causes gradual visual impairment over many months or years. It is responsible for 10 to 15 percent in of the blindness in the U.S. United States caused by macular degeneration.

The wet form of macular degeneration accounts for only to 10 to 15 percent of the disease, but is responsible for 80 percent of blindness. The wet form inflicts its ocular damage in a period of weeks or several months.

The prevalence of macular degeneration was extensively studied. It increases considerably as age advances. The overall prevalence of macular degeneration in the United States population above the age of 54 is 1.6 percent. When macular degeneration is computed per age groups, it is 0.0 percent below the age of 55, and 0.9 percent at the age of retirement 65. It Increases to 4.6 and 13.1 percent for those aged 75 and 85 respectively. Similar numbers were found in the United Kingdom, the Netherlands, and Australia. 1.7 million people in the US in 2010 were diagnosed with macular degeneration. The growing proportion of older adults in the US population is expected to more than double this number (3.8 million) in the next 30 years.

Multiple studies in the last 20 years uncovered some of the biological pathways that lead to the formation of retinal damage. These studies centered on the causes of cell death of the epithelial pigmented cells. Some of the current main findings are: Primary aging of the photoreceptors pigmented epithelial cells, Local activation of abnormal immune response and abnormal release of inflammatory cytokines against the retinal cells, Accumulation of connective tissue cells under Bruch's membrane with impaired inflammatory cytokines, Decreased elasticity end distensibility of the sclera, and Decreased in blood perfusion to the sub retinal space, leading to ischemia, atrophy, and cell death of the photoreceptors pigmented retinal cells. All these biological processes were found to play a role in the dry macular degeneration form.

The wet macular degeneration is dominated by an abnormal retinal response to the ischemia of the photoreceptors cells. The reduction in the capillary network and decline in capillary blood supply generates an abnormal and excessive production of cellular factors that enhance blood supply and increases blood perfusion to Bruch's membrane. These cytokines are the vascular growth factors or VGFs. Sixteen different vascular growth factors were isolated so far. They promote the creation of new blood vessels and increase the capillary network. They differ from each other by different binding affinity to their correspondent vascular growth receptors on the surface membrane of different blood vessel cells. The most potent of them is called VEGF. It is the one that binds to the vascular growth receptors on the surface of endothelial cell membranes.

Other risk factors such as genetic factors, inflammation, family history, ethnicity, and age were found to impact the prevalence of Macular Degeneration None of these factors can be modified by treatment. Smoking affects Macular Degeneration. Studies of smoking impact on vision revealed a substantial increase in prevalence progression and severity of Macular Degeneration. Alcohol use of 3 drinks a day or more, is an increased risk for Macular Degeneration. Age above the age of 55 is strongly associated with Macular Degeneration. Chronic use of aspirin is associated with increase in Macular Degeneration.

A diet rich in vegetables and fruits reduces the Macular Degeneration risk. Antioxidant vitamins and zinc are the most subscribed treatment for dry Macular Degeneration worldwide. The scientific basis for the antioxidant vitamins and zinc treatment was provided by the first of two large randomized placebo-controlled trials.

The Age Related Eye Disease Study (ARED1) randomized 3640 participants (aged 55 to 80) to 4 different clinical groups based on the presence of drusen in the retinal membrane (from none to extensive presence of drusen). Each treatment group was randomized to placebo treated and antioxidant vitamins, and zinc treated participants. The study duration was 6.3 years. The results of the ARED1 study were surprisingly limited. And as such, disappointing. Only participants with extensive macular lesions gained protective benefits by the use of antioxidant vitamins and zinc. All other participants, those who showed no lesions on study entry, or participants that were recruited with limited macular degenerative lesions, failed to gain any reduction in drusen number or obtained any protective benefits from the progression of the disease. Macular degeneration appeared or progressed in these groups of participants. The results of AREDS1 study implies that 11 patients with extensive macular lesion will need to be treated for seven years in order to prevent a progression in a single one.

AREDS2 enrolled and randomized 4201 participants to a five-year study. This time, two previously used antioxidants, vitamins beta carotene and tocopherol were withdrawn from the treatment protocol, and replaced by two different anti-oxidants, vitamins, lutein and zeaxanthin. Beta carotene was found to increase lung cancer, and vitamin E, tocopherol, is associated with increase in all-cause mortality. Omega 3 and Omega 6 (the known non-saturated fatty acids) were added as well. AREDS2, like ITS predecessor, ARDS1, failed to show different results. Neither the addition of two new antioxidants nor the addition of Omega acids, reduce the drusen number or prevented the progression of early dry non-exudative Macular Degeneration. The Two AREDS studies highlight the need for a new and efficient preventive method for the dry form of Macular Degeneration.

Early treatment studies by photodynamic laser have shown only small benefits in visual acuity. Later studies and a meta-analysis of 9 photocoagulation studies of drusen bodies removal revealed an increase in neo-vascularization but no decrease in the risk of visual loss. No reduction in progression to the geographic atrophy type of Macular Degeneration or blindness was achieved.

These data highlight the need and underline the necessity for a new mode of prevention, and a new mode of treatment for Macular Degeneration and in particular, for the non-exudative and the dry forms of Macular Degeneration.

Current treatment of the exudative form of Macular Degeneration includes: antioxidant vitamins and zinc; the use of photodynamic coagulation; and the use of trans vitreous injection of a VEGF inhibitor. Regardless of the mode of treatment, treatment of small and recent lesions is more effective in restoring vision than treatment of large and old.

The scientific basis for the use and benefits of antioxidant vitamin treatment in the wet form of Macular Degeneration is based on results achieved in AREDS1 and AREDS2 as well. An early wet lesion in one eye, or vision loss in the second eye were improved in 28 percent of participants with these findings. It also means that the majority of participants comprising of the rest (72 percent) did not receive any benefits from the same treatment.

Photodynamic therapy is also used in Macular Degeneration, e.g., wet macular degeneration. This mode of treatment is a sealing method of the leaking retinal capillaries. It consists of activating an injected photosensitive dye by a photo-activating laser beam through the eye. The endothelial damage produced by the dye free radicals release causes an intravascular thrombus that seals the vascular leak. The long term limitation of this treatment is disappointing. 33 present of the sealed vessels reopened in an 18 month follow up study. In spite of the photodynamic therapy. Continued neo-vascularization of the choroid membrane was observed. The use of laser photo dynamics therapy in the US, for the treatment of exudative macular degeneration has declined.

The main treatment today of exudative Macular Degeneration is the use of injected VEGF inhibitors. Four FDA approved VEGF inhibitors are available in the US with a narrow similar efficacy, but marked difference in price, dosage and frequency of administration. The results of VEGF treatment were assessed by multi-countries international retrospective study. Visual acuity was found to have improved for the first 3 months. It was followed by a progressive decline in visual acuity that required an increase in the number of injections. Only 37 percent of the treated patients achieved the target goal of 20/70. The best corrected visual acuity of another 30 percent is 20/200 or worse. Macular degeneration was detected in the majority of treated patients. The extent of the atrophy accurately reflected the amount of visual loss after 7 years. The need for continuous inhibition of VEGF over a 7 year period, implies that the cardinal stimulus of the disease, the suspected hypoxic ischemia, that drives the excessive production of VEGF in the retinal tissue, was not resolved even after 7 years of chronic VEGF inhibition.

SUMMARY OF THE INVENTION

These data highlight the marked limitation of the current mode of prevention, and the limited role of the current treatment of Macular Degeneration, in particular, the limitation of prevention and treatment of the exudative and non-exudative form of Macular Degeneration. No current FDA approved drug is known to relieve or block the primary ischemic Stimulus that propagates this disease. For the forgoing reasons, there is a need for a new mode of treatment for Macular Degeneration that increases the capillary network and augments capillary blood supply to enhance the tissue repair of the damaged retina.

For the forgoing reasons, there is a need for a new mode of prevention of Macular Degeneration that protects from retinal damage and prevents the symptoms of Macular Degeneration by increasing the capillary network and augmenting the capillary blood supply to the retina.

In particular, a method to prevent the retinal damage and the symptoms of retinal damage by increasing the blood supply and the capillary network to the macula where the lesion will form.

For the forgoing reasons, there is a need for a method that treats the retinal damage and the symptoms of retinal damage by increasing the capillary network and augments the capillary blood supply to the damaged retina to treat, enhance repair, and to heal the damaged retina and the symptoms of the damaged retina.

In particular, a method that treats the damaged macula and the symptoms of damaged macula by increasing the capillaries network and augmenting the capillary blood supply to the macula region where Macular Degenerative lesions were formed.

Accordingly, a method for preventing Macular Degeneration by direct administration of a pharmaceutical preparation of a Calcium Channel Blocker, an ACE Inhibitor or an Angiotensin Receptor Blocker to prevent the process and symptoms of Macular Degeneration is provided.

The term "Macular Degeneration" as used herein is a broad term, and is meant to refer to any process in the eye that cause the appearance and symptoms of Macular Degeneration.

Accordingly, in a generally applicable first aspect (i.e., independently combinable with any of the aspects or embodiments identified herein), the Calcium Channel Blocker, ACE Inhibitor, or Angiotensin Receptor Blocker may be administered directly to the macular area of the retina before symptoms form to prevent Macular Degeneration. For example, in men or women with normal macula before the degenerative process started.

In a generally applicable embodiment (i.e., independently combinable with any of the aspects or embodiments identified herein) of the first aspect, the Calcium Channel Blocker, ACE Inhibitor, or Angiotensin Receptor Blocker may be administered directly to the macular area of the retina to treat and heal the symptoms of Macular Degeneration.

In a generally applicable embodiment (i.e., independently combinable with any of the aspects or embodiments identified herein) of the first aspect, the Calcium Channel Blocker, ACE Inhibitor, or Angiotensin Receptor Blocker may be administered even after the Macular Degeneration has dissipated and the macular membrane has healed to prevent the recurrence.

Calcium Channel Blockers, ACE Inhibitors, and Angiotensin Receptor Blockers are classes of pharmaceutical drugs when taken orally they dilate the arteriolar system by blocking the activity of the calcium channel receptors, ACE receptors or angiotensin receptors.

Contact Calcium Channel Blockers, ACE Inhibitors, and Angiotensin Receptor Blockers are a new class of pharmaceutical products. When applied directly to target tissue they increase the capillary network, augment the capillary blood supply, and enhance tissue repair in diverse body membrane tissues.

Currently, there are over 20 pharmaceutical patented ACE Inhibitor or Angiotensin Receptor Blocker drugs that use this property to treat hypertension, and congestive heart failure. The clinical indication of ACE Inhibitors or Angiotensin Receptor Blockers is therefore currently limited to the field of cardiovascular diseases.

Calcium Channel Blockers, ACE Inhibitors and Angiotensin Receptor Blockers were extensively studied but their ability to prevent and treat Macular Degeneration remained unknown.

The use of application of Calcium Channel Blockers, ACE Inhibitors or Angiotensin Receptor Blockers to the eye macular membrane space is provided. The direct contact with the retinal tissue and in particular the macular region, increases the capillary network and augments the blood supply to the retina, and in particular, increases the capillary network and augments the blood supply to the macular territory.

The new class may be used for the prevention and treatment of Macular Degeneration or other syndromes associated with Macular Degeneration.

No trial of Calcium Channel Blockers, ACE Inhibitors or Angiotensin Receptor Blockers for the prevention or treatment of Macular Degeneration was ever published.

DETAILED DESCRIPTION OF THE INVENTION

The following discussion addresses a number of embodiments and applications of the present disclosure. The beneficial features of the present disclosure will be evident from the described embodiments. It is to be understood that the present disclosure is not limited to such specific applications and that numerous implementations of the present disclosure may be realized. All references to patents, patent applications, and non-patent publications mentioned in the specification are hereby incorporated by reference, in their entireties.

Contact neo-vasodilators are a new class of medication. This invention describes the use of contact neo-vasodilators such as Valsartan, a known Angiotensin Receptor Blocker or Enalapril, a known ACE Inhibitor, or calcium channel blockers used in the treatment of hypertension and congestive heart failure, for the prevention and treatment of Macular Degeneration.

ACE Inhibitors such as enalapril, benazepril, lisinopril, ramipril, or fosinopril or Angiotensin Receptor Blockers such as Valsartan, telmisartan, olmesartan, losartan, irbesartan, candesartan and azilsartan, when administered directly to the eye, they are very effective drugs for the prevention of Macular Degeneration syndrome, and in particular, age-related Macular Degeneration syndrome.

Valsartan, or other Angiotensin Receptor Blockers, or Enalapril, or other ACE Inhibitors are drugs which previously may have been used in treatment of high blood pressure and or congestive heart failure, when applied in a pharmacological composition in an effective amount, directly into the eye, by direct administration or intravitreal injection, they are effective drugs for the treatment of Macular Degeneration.

Angiotensin Receptor Blockers such as Valsartan, telmisartan, olmesartan, losartan, irbesartan, candesartan and azilsartan, when administered directly to the eye, they are very effective drugs for the prevention of Macular Degeneration.

Pharmacological composition as used herein is a pharmaceutical preparation according to the invention, composed but not limited to ACE Inhibitors, Calcium Channel Blockers, or Angiotensin Receptor Blockers and a suitable non-toxic pharmaceutical carrier.

Effective amount as used herein is an amount of the pharmaceutical composition of Calcium Channel Inhibitors, ACE Inhibitors, or Angiotensin Receptor Blockers that is effective for treating the Macular Degeneration syndrome. An amount of Calcium Channel Inhibitors, ACE Inhibitors, or Angiotensin Receptor Blockers that is suitable for direct administration or intravitreal injection to the eye.

A method is provided of applying a pharmaceutical preparation in an effective amount of one or more vasodilators (e.g., calcium channel blockers, ACE inhibitors, angiotensin receptor blockers, nitrates, alpha blockers, beta blockers, hydralazine, and/or angiotensin receptor-neprilysin inhibitors), directly to the tissue of the eye or into the eye via intraocular injection to treat or prevent macular generation.

A method is provided of applying a pharmacological composition in an effective amount, of one or more vasodilators (e.g., calcium channel blockers, ACE inhibitors, angiotensin receptor blockers, nitrates, alpha blockers, beta blockers, hydralazine, and/or angiotensin receptor-neprilysin inhibitors), directly to the tissue of the eye or into the eye via intraocular injection to treat or prevent wet or dry macular generation.

The pharmacological preparation can comprise a calcium channel blocker. The calcium channel blocker can be in a suitable nontoxic pharmacological carrier.

The pharmacological preparation can comprise an ACE inhibitor. The ACE inhibitor can be in a suitable nontoxic pharmacological carrier.

The pharmacological preparation can comprise an angiotensin receptor blocker. The angiotensin receptor blocker can be in a suitable nontoxic pharmacological carrier.

An effective amount for treatment or prevention of macular degeneration is administered. An amount of calcium channel blocker that is suitable for treatment by absorption through the epidermis of the area where the pressure ulcer is located is administered.

An effective amount for treatment or prevention of macular degeneration is administered. An amount of ACE inhibitor that is suitable for treatment by intraocular injection or direct application to the tissue of the eye is administered.

An effective amount for treatment or prevention of macular degeneration is administered. An amount of angiotensin receptor blocker that is suitable for treatment by intraocular injection or direct application to the tissue of the eye is administered.

Contact vasodilators (e.g., calcium channel blockers, ACE inhibitors, angiotensin receptor blockers, nitrates, alpha blockers, beta blockers, hydralazine, and/or angiotensin receptor-neprilysin inhibitors) are a new class of pharmaceutical medications that increase blood supply, which produces biological changes.

In the case of treatment or prevention of macular degeneration, these changes can include one or more of increasing the blood supply to the macula.

Calcium channel blockers are a new class of pharmaceutical drugs that disrupt the entry of calcium molecules through the L type voltage operated channels to cardiac muscle and blood vessels cells. The blockage of calcium entry causes the relief of arterial spasm.

Currently there are 70 pharmaceutical patented calcium channel blocker drugs that use this property to treat hypertension, angina pectoris and cardiac arrhythmia. The clinical indication for the therapeutic use of calcium channel blockers was therefore limited, until now, to the field of cardiovascular diseases only.

Calcium channel blockers were extensively studied but their ability to prevent and or to treat macular degeneration remained heretofore unknown.

Accordingly, new uses are provided of contact-applied calcium channel blockers for application to the tissue of the eye or for intraocular injection. The new use may be used for the prevention or treatment of macular degeneration. No trial of topical calcium channel blockers for the prevention or treatment of macular degeneration has heretofore been published.

Contact calcium channel blockers are a part of contact-vasodilators, a new class of medication. The use is provided of contact neo-vasodilators such as Nifedipine, a known calcium channel blocker used in the treatment of hypertension, for the prevention and treatment macular degeneration.

Nifedipine, Amlodipine, Felodipine, Isradipine, Nicardipine, Nisoldipine and Clevidipine are in a class of dihydropyridines calcium channel blockers. Verapamil and Diltiazem are non-dihydropyridines calcium channel blockers. When applied by contact these are very effective drugs for the treatment or prevention of macular degeneration.

Inhibitors of angiotensin converting enzyme (ACE) can be employed as vasodilators. Angiotensin II is a chemical produced by the body that primarily circulates in the blood. It causes the muscles surrounding blood vessels to contract, thereby narrowing the vessels. Angiotensin II is formed from angiotensin I in the blood by the enzyme angiotensin converting enzyme (ACE). Angiotensin I in the blood is itself formed from angiotensinogen, a protein produced by the liver and released into the blood. Angiotensin converting enzyme inhibitors (ACE inhibitors) are medications that slow (inhibit) the activity of the enzyme ACE, which decreases the production of angiotensin II. As a result, blood vessels enlarge or dilate. ACE inhibitors include, but are not limited to benazepril (Lotensin), captopril (Capoten), enalapril (Vasotec, Epaned, Lexxel), fosinopril (Monopril), lisinopril (Prinivil), moexipril (Univasc), perindopril (Aceon), quinapril (Accupril), ramipril (Altace), and trandolapril (Mavik).

Angiotensin II receptor blockers (ARBs) help relax the blood vessels. Angiotensin II receptor blockers block the action of angiotensin II, allowing blood vessels to dilate. Angiotensin receptor blockers include, but are not limited to: azilsartan (Edarbi), candesartan (Atacand), eprosartan, irbesartan (Avapro), losartan (Cozaar), olmesartan (Benicar), telmisartan (Micardis), and valsartan (Diovan).

Other vasodilators are known in the art. These include, but are not limited to nitrates (nitroglycerin, isosorbide mononitrate and isosorbide dinitrate), Alpha blockers (doxazosin (Cardura), prazosin (Minipress), terazosin), Beta blockers (Acebutolol (Sectral), Atenolol (Tenormin), Bisoprolol fumarate (Zebeta), Carvedilol (Coreg)—Combined alpha/beta blocker, Esmilol (Brevibloc), Labetalol (Trandate, Normodyne)—Combined alpha/beta blocker, Metoprolol tartrate (Lopressor) and metoprolol succinate (Toprol-XL), Nadolol (Corgard), Nebivolol (Bystolic), Penbutolol sulfate (Levatol), Propranolol (Inderal), Sotalol (Betapace), HCTZ and bisoprolol (Ziac) is a beta blocker plus diuretic), Hydralazine, and angiotensin receptor-neprilysin inhibitors (ARNi) (Entresto, sacubitril/valsartan).

Conditions Amenable to Treatment or Prevention

Compositions and methods are provided for the prevention or treatment of macular degeneration, e.g., for the treatment or prevention of wet or dry macular degeneration.

Application of vasodilators (e.g., calcium channel blockers, ACE inhibitors, angiotensin receptor blockers, nitrates, alpha blockers, beta blockers, hydralazine, and/or angiotensin receptor-neprilysin inhibitors), such as Nifedipine or other calcium channel blockers, which previously may have been used in the treatment of high blood pressure, in a pharmacological composition, in an effective amount, in a contact form, such as, but not limited to an oil, liquid preparation or suspension, to the tissue of the eye or for administration by intraocular injection, can be employed to treat or prevent the symptoms of macular degeneration.

Pharmacological compositions of the embodiments include but are not limited to one or more vasodilators (e.g., calcium channel blockers, ACE inhibitors, angiotensin receptor blockers, nitrates, alpha blockers, beta blockers, hydralazine, and/or angiotensin receptor-neprilysin inhibitors) and a suitable non toxic pharmaceutical carrier. The pharmaceutical composition in administered in an amount effective for treating macular degeneration, e.g., an amount suitable for treatment by direct application to tissue of the eye or by intraocular injection.

Macular degeneration, e.g., wet macular degeneration, dry macular degeneration, associated symptoms, and treatment thereof, are described in the following references, each of which is incorporated by reference herein in its entirety and each of which is hereby made a part of this specification: Lord S R, Dayhew J. Visual risk factors for falls in older people. J Am Geriatr Soc 2001; 49:508; Bressler N M. Age-related macular degeneration is the leading cause of blindness. JAMA 2004; 291:1900; Yang Z, Stratton C, Francis P J, et al. Toll-like receptor 3 and geographic atrophy in age-related macular degeneration. N Engl J Med 2008; 359:1456; Holz F G, Wolfensberger T J, Piguet B, et al. Bilateral macular drusen in age-related macular degeneration. Prognosis and risk factors. Ophthalmology 1994; 101: 1522; Ferris F L, Davis M D, Clemons T E, et al. A simplified severity scale for age-related macular degeneration: AREDS Report No. 18. Arch Ophthalmol 2005; 123: 1570; Gass J D, Agarwal A, Lavina A M, Tawansy K A. Focal inner retinal hemorrhages in patients with drusen: an early sign of occult choroidal neovascularization and chorioretinal anastomosis. Retina 2003; 23:741; Bressler N M. Age-related macular degeneration is the leading cause of blindness. JAMA 2004; 291:1900; Owen C G, Jarrar Z, Wormald R, et al. The estimated prevalence and incidence of late stage age related macular degeneration in the UK. Br J Ophthalmol 2012; 96:752; Keel S, Xie J, Foreman J, et al. Prevalence of Age-Related Macular Degeneration in Australia: The Australian National Eye Health Survey. JAMA Ophthalmol 2017; 135:1242; Rein D B, Wittenborn J S, Zhang X, et al. Forecasting age-related macular degeneration through the year 2050: the potential impact of new treatments. Arch Ophthalmol 2009; 127:533; Zarbin M A. Age-related macular degeneration: review of pathogenesis. Eur J Ophthalmol 1998; 8:199; Yang Z, Stratton C, Francis P J, et al. Toll-like receptor 3 and geographic atrophy in age-related macular degeneration. N Engl J Med 2008; 359:1456; Brown D M, Kaiser P K, Michels M, et al. Ranibizumab versus verteporfin for neovascular age-related macular degeneration. N Engl J Med 2006; 355:1432; Seddon J M, George S, Rosner B, Rifai N. Progression of age-related macular degeneration: prospective assessment of C-reactive protein, interleukin 6, and other cardiovascular biomarkers. Arch Ophthalmol 2005; 123:774; Friedman E, Ivry M, Ebert E, et al. Increased scleral rigidity and age-related macular degeneration. Ophthalmology 1989; 96:104; Grunwald J E, Metelitsina T I, Dupont J C, et al. Reduced foveolar choroidal blood flow in eyes with increasing AMD severity. Invest Ophthalmol Vis Sci 2005; 46:1033; Friedman E, Krupsky S, Lane A M, et al. Ocular blood flow velocity in age-related macular degeneration. Ophthalmology 1995; 102:640; Bhisitkul R B, Mendes T S, Rofagha S, et al. Macular atrophy progression and 7-year vision outcomes in subjects from the ANCHOR, MARINA, and HORIZON studies: the SEVEN-UP study. Am J Ophthalmol 2015; 159:915; Ferrara N. Vascular endothelial growth factor: basic science and clinical progress. Endocr Rev 2004; 25:581; Despriet D D, van Duijn C M, Oostra B A, et al. Complement component C3 and risk of age-related macular degeneration. Ophthalmology 2009; 116:474; Stone E M, Braun T A, Russell S R, et al. Missense variations in the fibulin 5 gene and age-related macular degeneration. N Engl J Med 2004; 351:346; Klein R, Knudtson M D, Klein B E, et al. Inflammation, complement factor h, and age-related macular degeneration: the Multi-ethnic Study of Atherosclerosis. Ophthalmology 2008; 115:1742; Klein B E, Klein R, Lee K E, et al. Risk of incident age-related eye diseases in people with an affected sibling: The Beaver Dam Eye Study. Am J Epidemiol 2001; 154:207; Klein R, Rowland M L, Harris M I. Racial/ethnic differences in age-related maculopathy. Third National Health and Nutrition Examination Survey. Ophthalmology 1995; 102:371; Weih L M, VanNewkirk M R, McCarty C A, Taylor H R. Age-specific causes of bilateral visual impairment. Arch Ophthalmol 2000; 118:264; Klein R, Klein B E, Moss S E. Relation of smoking to the incidence of age-related maculopathy. The Beaver Dam Eye Study. Am J Epidemiol 1998; 147:103; Khan J C, Thurlby D A, Shahid H, et al. Smoking and age related macular degeneration: the number of pack years of cigarette smoking is a major determinant of risk for both geographic atrophy and choroidal neovascularisation. Br J Ophthalmol 2006; 90:75; Chong E W, Kreis A J, Wong T Y, et al. Alcohol consumption and the risk of age-related macular degeneration: a systematic review and meta-analysis. Am J Ophthalmol 2008; 145:707; Mares J A, Voland R P, Sondel S A, et al. Healthy lifestyles related to subsequent prevalence of age-related macular degeneration. Arch Ophthalmol 2011; 129:470; Despriet D D, van Duijn C M, Oostra B A, et al. Complement component C3 and risk of age-related macular degeneration. Ophthalmology 2009; 116:474; Age-Related Eye Disease Study Research Group. A randomized, placebo-controlled, clinical trial of high-dose supplementation with vitamins C and E, beta carotene, and zinc for age-related macular degeneration and vision loss: AREDS report no. 8. Arch Ophthalmol 2001; 119:1417; Age-Related Eye Disease Study 2 Research Group. Lutein+ zeaxanthin and omega-3 fatty acids for age-related macular degeneration: the Age-Related Eye Disease Study 2 (AREDS2) randomized clinical trial. JAMA 2013; 309: 2005; Ho A C, Maguire M G, Yoken J, et al. Laser-induced drusen reduction improves visual function at 1 year. Choroidal Neovascularization Prevention Trial Research Group. Ophthalmology 1999; 106:1367; Friberg T R, Musch D C, Lim J I, et al. Prophylactic treatment of age-related macular degeneration report number 1: 810-nanometer laser to eyes with drusen. Unilaterally eligible patients. Ophthalmology 2006; 113:622.el; Virgili G, Michelessi M, Parodi M B, et al. Laser treatment of drusen to prevent progression to advanced age-related macular degeneration. Cochrane Database Syst Rev 2015; CD006537; Antoszyk A N, Tuomi L, Chung C Y, et al. Ranibizumab combined with verteporfin photodynamic therapy in neovascular age-related macular degeneration (FOCUS): year 2 results. Am J Ophthalmol 2008; 145:862; Rosenfeld P J, Brown D M, Heier J S, et al. Ranibizumab for neovascular age-related macular degeneration. N Engl J Med 2006; 355:1419; Rofagha S, Bhisitkul R B, Boyer D S, et al. Seven-year outcomes in ranibizumab-treated patients in ANCHOR, MARINA, and HORIZON: a multicenter cohort study (SEVEN-UP). Ophthalmology 2013; 120:2292; Lawrenson J G, Evans J R. Omega 3 fatty acids for preventing or slowing the progression of age-related macular degeneration. Cochrane Database Syst Rev 2015; CD010015; Smith W, Assink J, Klein R, et al. Risk factors for age-related macular degeneration: Pooled findings from three continents. Ophthalmology 2001; 108:697; Williams, B., Drug discovery in renin-angiotensin system intervention: past and future. Therapeutic Advances in Cardiovascular Disease, 2016 June; 10(3): 118-25; Shi L, Mao C, Xu Z, Zhang L. Angiotensin-converting enzymes and drug discovery in cardiovascular disease. Drug Discovery today, 2010, May 1;15(9-10):332-41; Jager, R D, Miler, W F, Miller, J W. Age Related Macular Degeneration; New England Journal of Medicine; 2008; 358 (24) 2606; Klein, B E, Howard K P, Gangnon, R E, Dreyer, J O, Lee, K E, Klein, R: Long term use of aspirin and age related macular degeneration. 2012, JAMA DES; 308 (23) 2469-78; Godfraind, T., 2017. Discovery and development of calcium channel blockers. Frontiers in pharmacology, 8, p. 286.

Compositions including one or more vasodilators (e.g., calcium channel blockers, ACE inhibitors, angiotensin receptor blockers, nitrates, alpha blockers, beta blockers, hydralazine, and/or angiotensin receptor-neprilysin inhibitors), optionally in combination with conventional therapies, and associated methods for treatment of macular degeneration and related symptoms are provided.

Some embodiments relate to a pharmaceutical composition and method of treatment using the pharmaceutical composition, wherein the pharmaceutical composition comprises at least one calcium channel blocker, for example, a calcium channel blocker selected from the group consisting of amlodipine (Norvasc), diltiazem (Cardizem LA, Tiazac), felodipine (Plendil), isradipine (Dynacirc), nifedipine (Adalat, Procardia), nicardipine (Cardene), nimodipine (Nimotop), nisoldipine (Sular), verapamil (Covera-HS, Verelan PM, Calan), verapamil, diltiazem and nicardipine (Cardene IV). Some embodiments relate to a pharmaceutical composition and method of treatment using the pharmaceutical composition, wherein the pharmaceutical composition comprises at least one ACE inhibitors, for example at least one ACE inhibitor selected from the group consisting of benazepril (Lotensin), captopril (Capoten), enalapril (Vasotec, Epaned, Lexxel), fosinopril (Monopril), lisinopril (Prinivil), moexipril (Univasc), perindopril (Aceon), quinapril (Accupril), ramipril (Altace), and trandolapril (Mavik). Some embodiments relate to a pharmaceutical composition and method of treatment using the pharmaceutical composition, wherein the pharmaceutical composition comprises at least one angiotensin receptor blocker, for example at least one angiotensin receptor blocker selected from the group consisting of azilsartan (Edarbi). candesartan (Atacand), eprosartan, irbesartan (Avapro), losartan (Cozaar), olmesartan (Benicar), telmisartan (Micardis), and valsartan (Diovan). In certain embodiments, the pharmaceutical composition is in a form suitable for contact administration, e.g., to tissue of the eye or by intraocular administration, however other routes of administration are also considered that involve contact of the vasodilator to the tissue to be treated.

The pharmaceutical compositions for treatment of macular degeneration can further comprise other pharmaceutically active ingredients. These can include drugs to control pain, for example, nonsteroidal anti-inflammatory drugs such as ibuprofen or naproxen sodium, topical anesthetics such as lidocaine, drugs to fight infections (e.g., antibiotic, antiviral, or antifungal agents). The treatment can be administered in conjunction with other therapies, e.g., the conventional therapies for macular degeneration as described elsewhere herein.

The use of topical vasodilators (e.g., calcium channel blockers, ACE inhibitors, angiotensin receptor blockers, nitrates, alpha blockers, beta blockers, hydralazine, and/or angiotensin receptor-neprilysin inhibitors) for treatment of macular degeneration is a new class of drugs. The new class may be used for wet macular degeneration, dry macular degeneration, or to enhance efficacy of conventional macular degeneration drugs.

In one method of the vasodilator may be applied directly to the tissue of the eye, e.g., in a form of an eyedrop.

In another embodiment, the vasodilator may be injected directly into the intraocular space to treat macular degeneration. The vasodilator may be applied even after the macular degeneration has been ameliorated to prevent recurrence of macular degeneration.

Definitions

The term "alcohol" as used herein is a broad term, and is to be given its ordinary and customary meaning to a person of ordinary skill in the art (and is not to be limited to a special or customized meaning), and refers without limitation to any compound as described herein incorporating one or more hydroxy groups, or being substituted by or functionalized to include one or more hydroxy groups.

The term "derivative" as used herein is a broad term, and is to be given its ordinary and customary meaning to a person of ordinary skill in the art (and is not to be limited to a special or customized meaning), and refers without limitation to any compound as described herein incorporating one or more derivative groups, or being substituted by or functionalized to include one or more derivative groups. Derivatives include but are not limited to esters, amides, anhydrides, acid halides, thioesters, and phosphates.

The term "hydrocarbon" as used herein is a broad term, and is to be given its ordinary and customary meaning to a person of ordinary skill in the art (and is not to be limited to a special or customized meaning), and refers without limitation to any moiety comprising only carbon and hydrogen atoms. A functionalized or substituted hydrocarbon moiety has one or more substituents as described elsewhere herein.

The term "lipid" as used herein is a broad term, and is to be given its ordinary and customary meaning to a person of ordinary skill in the art (and is not to be limited to a special or customized meaning), and refers without limitation to saturated and unsaturated oils and waxes, derivatives, amides, glycerides, fatty acids, fatty alcohols, sterol and sterol derivatives, tocopherols, carotenoids, among others.

The terms "pharmaceutically acceptable" as used herein is a broad term, and is to be given its ordinary and customary meaning to a person of ordinary skill in the art (and is not to be limited to a special or customized meaning), and refers without limitation to those compounds, materials, compositions, and/or dosage forms which are, within the scope of sound medical judgment, suitable for contact with the tissues of and/or for consumption by human beings and animals without excessive toxicity, irritation, allergic response, or other problem complications commensurate with a reasonable risk/benefit ratio.

The terms "pharmaceutically acceptable salts" and "a pharmaceutically acceptable salt thereof" as used herein are broad terms, and are to be given their ordinary and customary meaning to a person of ordinary skill in the art (and is not to be limited to a special or customized meaning), and refer without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity. In addition to salts, pharmaceutically acceptable precursors and derivatives of the compounds can be employed. Pharmaceutically acceptable amides, lower alkyl derivatives, and protected derivatives can also be suitable for use in compositions and methods of preferred embodiments. While it may be possible to administer the compounds of the preferred embodiments in the form of pharmaceutically acceptable salts, it is generally preferred to administer the compounds in neutral form.

The term "pharmaceutical composition" as used herein is a broad term, and is to be given its ordinary and customary meaning to a person of ordinary skill in the art (and is not to be limited to a special or customized meaning), and refers without limitation to a mixture of one or more pharmacologically active ingredients (e.g. vasodilators) disclosed herein with other chemical components, such as diluents or carriers. The pharmaceutical composition facilitates administration of the compound to an organism. Pharmaceutical compositions can also be obtained by reacting compounds with inorganic or organic acids or bases. Pharmaceutical compositions will generally be tailored to the specific intended route of administration.

As used herein, a "carrier" as used herein is a broad term, and is to be given its ordinary and customary meaning to a person of ordinary skill in the art (and is not to be limited to a special or customized meaning), and refers without limitation to a compound that facilitates the incorporation of a compound into cells or tissues. For example, without limitation, dimethyl sulfoxide (DMSO) is a commonly utilized carrier that facilitates the uptake of many organic compounds into cells or tissues of a subject. Water, saline solution, ethanol, and mineral oil are also carriers employed in certain pharmaceutical compositions.

As used herein, a "diluent" as used herein is a broad term, and is to be given its ordinary and customary meaning to a person of ordinary skill in the art (and is not to be limited to a special or customized meaning), and refers without limitation to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" as used herein is a broad term, and is to be given its ordinary and customary meaning to a person of ordinary skill in the art (and is not to be limited to a special or customized meaning), and refers without limitation to a substance that is added to a pharmaceutical composition to provide, without limitation, bulk, consistency, stability, binding ability, lubrication, disintegrating ability etc., to the composition. A "diluent" is a type of excipient.

As used herein, a "subject" as used herein is a broad term, and is to be given its ordinary and customary meaning to a person of ordinary skill in the art (and is not to be limited to a special or customized meaning), and refers without limitation to an animal that is the object of treatment, observation or experiment. "Animal" includes cold- and warm-blooded vertebrates and invertebrates such as fish, shellfish, reptiles, and, in particular, mammals. "Mammal" includes, without limitation, dolphins, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" are broad terms, and are to be given their ordinary and customary meaning (and are not to be limited to a special or customized meaning) and, without limitation, do not necessarily mean total cure or abolition of the disease or condition. Any alleviation of any undesired markers, signs or symptoms of a disease or condition, to any extent, can be considered treatment and/or therapy. Furthermore, treatment may include acts that may worsen the patient's overall feeling of well-being or appearance.

The terms "therapeutically effective amount" and "effective amount" as used herein are broad terms, and are to be given its ordinary and customary meaning to a person of ordinary skill in the art (and are not to be limited to a special or customized meaning), and are used without limitation to indicate an amount of an active compound, or pharmaceutical agent, that elicits the biological or medicinal response indicated. For example, a therapeutically effective amount of compound can be the amount needed to prevent, alleviate or ameliorate markers or symptoms of a condition or prolong the survival of the subject being treated. This response may occur in a tissue, system, animal or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The term "solvents" as used herein is a broad term, and is to be given its ordinary and customary meaning to a person of ordinary skill in the art (and is not to be limited to a special or customized meaning), and refers without limitation to compounds with some characteristics of solvency for other compounds or means, that can be polar or nonpolar, linear or branched, cyclic or aliphatic, aromatic, naphthenic and that includes but is not limited to: alcohols, derivatives, diesters, ketones, acetates, terpenes, sulfoxides, glycols, paraffins, hydrocarbons, anhydrides, heterocyclics, among others.

It is to be understood that where compounds disclosed herein (e.g., calcium channel blockers, ACE inhibitors, angiotensin receptor blockers, nitrates, alpha blockers, beta blockers, hydralazine, and/or angiotensin receptor-neprilysin inhibitors) have unfilled valencies, then the valencies are to be filled with hydrogens or isotopes thereof, e.g., hydrogen-1 (protium) and hydrogen-2 (deuterium).

It is understood that the compounds described herein (e.g., calcium channel blockers, ACE inhibitors, angiotensin receptor blockers, nitrates, alpha blockers, beta blockers, hydralazine, and/or angiotensin receptor-neprilysin inhibitors) can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein may include crystalline forms (also known as polymorphs, which include the different crystal packing arrangements of the same elemental composition of a compound), amorphous phases, salts, solvates, and hydrates, e.g., of vasodilators. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein (e.g., vasodilators) may exist in unsolvated as well as solvated forms. In general, the solvated forms are considered equivalent to the unsolvated forms for the purposes of the compounds and methods provided herein.

Where a range of values is provided, it is understood that the upper and lower limit, and any intervening value between the upper and lower limit of the range is included.

Any percentages, ratios or other quantities referred to herein are on a weight basis, unless otherwise indicated.

Pharmaceutical Compositions

The vasodilators (e.g., calcium channel blockers, ACE inhibitors, angiotensin receptor blockers, nitrates, alpha blockers, beta blockers, hydralazine, and/or angiotensin receptor-neprilysin inhibitors) can be prepared by any suitable method known to those in the art. For representative methods, see, for example, Francis A. Carey et al., Advanced Organic Chemistry: Part B: Reaction and Synthesis (5$^{th}$ Ed. 2005).

Formulations including a vasodilator (e.g., a calcium channel blocker, ACE inhibitor and/or angiotensin receptor blocker) and at least one excipient are provided. It is generally preferred to administer the compounds of the embodiments in topical formulations; however, other routes of administration are also contemplated.

The pharmaceutical compositions described herein can be administered by themselves to a subject, or in compositions where they are mixed with other active agents, as in combination therapy, or with carriers, diluents, excipients or combinations thereof. Formulation is dependent upon the route of administration chosen. Techniques for formulation and administration of the compounds described herein are known to those skilled in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

The pharmaceutical compositions disclosed herein may be manufactured by a process that is itself known, e.g., by means of conventional mixing, dissolving, granulating, dragee-making, levigating, emulsifying, encapsulating, entrapping, tableting, or extracting processes. Many of the vasodilator (e.g., a calcium channel blocker, ACE inhibitor and/or angiotensin receptor blocker) used in the pharmaceutical combinations disclosed herein may be provided as salts with pharmaceutically acceptable counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Contemplated herein is any combination of the forgoing, or other methods as would be known to one of ordinary skill in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

The compositions described herein are suitable for use in treatment or prevention of macular degeneration or associated symptoms. The compositions are suitable for use in any patient where treatment or prevention of macular degeneration is desirable.

The vasodilator (e.g., a calcium channel blocker, ACE inhibitor and/or angiotensin receptor blocker) can be employed in various types of formulations. Topical formulations including one or more vasodilators in combination with at least one excipient are provided. Excipients can include a nonaqueous or aqueous carrier, and one or more agents selected from moisturizing agents, pH adjusting agents, deodorants, fragrances, chelating agents, preservatives, emulsifiers, thickeners, solubilizing agents, penetration enhancers, anti-irritants, colorants, surfactants, beneficial agents, pharmaceutical agents, and other components as known in the art for use in connection with topical formulations for application to skin or ocular membranes. The formulation can be provided as an aqueous formulation, or in an anhydrous formulation which may prevent water-based irritant contact dermatitis or stinging sensation upon application. In another embodiment, the composition is formulated such that preservatives need not be employed (e.g., a preservative-free formulation) so as to avoid skin irritation associated with certain preservatives.

To facilitate application, the composition may be provided as an ointment, an oil, a lotion, a paste, a powder, a gel, or a cream. The composition may also include additional ingredients such as a protective agent, an emollient, a humectant, an antibiotic agent, an antifungal agent, an antiviral agent, an antiprotozoal agent, an anesthetic agent, a steroidal anti-inflammatory agent, a non-steroidal anti-inflammatory agent, an antipruritic agent, an antioxidant agent, an anti-histamine agent, a vitamin or vitamin complex, a hormone, an anti-skin atrophy agent, and combinations thereof. In a further embodiment, the composition may avoid animal or cellular-based materials to avoid irritation. The composition can be applied directly to the tissue of the eye.

Methods of using vasodilator formulations are provided. The compositions may be applied topically, but may also be applied to the macula via intraocular injection.

Some embodiments include administering vasodilator (e.g., a calcium channel blocker, ACE inhibitor and/or angiotensin receptor blocker) compositions provided herein in topical formulations; however, other routes of administration are also contemplated (e.g., intraocular or the like). Contemplated routes of administration include but are not limited to topical and intraocular. Suitable liquid forms include suspensions, emulsions, solutions, and the like. Unit dosage forms can also be provided, e.g., individual packets with a premeasured amount of the formulation, configured for administration to the tissue on a predetermined schedule (e.g., daily, weekly, etc.). Unit dosage forms configured for administration twice a day can be employed; however, in certain embodiments it can be desirable to configure the unit dosage form for administration once a day, four times a day, or more, or once every other day, every three days, weekly, or less, or on an as-needed basis.

In some embodiments, the topical and intraocular formulations typically comprise from about 0.001 wt. % or less to about 50 wt. % or more of active ingredient, such as the vasodilator (e.g., a calcium channel blocker, ACE inhibitor and/or angiotensin receptor blocker), preferably from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Compositions and formulations for topical administration to the tissue of the eye can include gels, drops, sprays, liquids, and aerosols. Conventional pharmaceutical carriers, aqueous or oily bases, thickeners and the like may be employed. Such formulations are typically provided in an eyedropper. A liquid or gel can also be placed using an applicator, e.g., a wand, a sponge, a syringe, or other suitable method.

A topical formulation can be provided in a form of a carrier containing the vasodilator, e.g., 50 ppm or less to 1000, 5000, 10000, 50000, 100000, 500000 ppm or more of the vasodilator. The topical formulation can contain from 0.01 wt. % or less (e.g., 0.001 wt. %) to 10 wt. % or more, e.g., 0.01 wt. % to 0.02 wt. %, 0.03 wt. %, 0.04 wt. %, 0.05 wt. %, 0.1 wt. %, 1 wt. % to 5 wt. % or 10 wt. % or 20 wt. % of the vasodilator. The amount of vasodilator in the base can be adjusted up or down.

Liquids and gels containing the vasodilator, optionally with other components as described herein, can be prepared using techniques as are known in the art for preparing topical compositions. See, e.g., Handbook of Cosmetic Science and Technology, Fourth Edition, edited by André O. Barel, Marc Paye, Howard I. Maibach, CRC Press, 2014, the contents of which is hereby incorporated by reference in its entirety. Various formulations are possible.

For liquid formulations (e.g., gel or lotion forms), a silicone, e.g., a cyclosiloxane or linear silicone (e.g., silicone elastomer), can be employed as a carrier. One type of suitable carrier is a dimethicone crosspolymer gel, e.g., dimethicone crosspolymer in cyclopentasiloxane. Other suitable dimethicone crosspolymers include cyclopentasiloxane, dimethicone/vinyldimethicone crosspolymer; dimethicone, dimethicone/vinyl dimethicone crosspolymer; and isodecane dimethicone/vinyl dimethicone crosspolymer.

Typically, the carrier is present in an amount of from about 80 wt. % to about 95 wt. %, or 82 wt. % to 92 wt. %, e.g., in a topical formulation for application to skin.

Penetration enhancers can be employed to enhance penetration of the vasodilator into tissue. Typical amounts when employed in topical formulations are from 1% by weight to 4% by weight. Typical amounts for anti-irritation agents when employed in topical formulations are from 1% by weight to 4% by weight. Typical amounts for anti-inflammatory agents when employed in topical formulations are from 1% by weight to 4% by weight. Typical amounts for anti-inflammatory agents when employed in topical formulations are from 0.1% by weight to 2% by weight.

In some embodiments, the vasodilator can be in admixture with a suitable carrier, diluent, or excipient, and can contain auxiliary substances such as wetting or emulsifying agents, pH buffering agents, gelling or viscosity enhancing additives, preservatives, scenting agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulations include, without limitation, monoglycerides, diglycerides, sulfatides, lysolecithin, phospholipids, saponin, bile acids, and the like. The presence of such additional components can influence the physical state, solubility, stability, rate of release, rate of clearance, and penetration of active ingredients.

The compositions for topical administration to the tissue of the eye comprise the vasodilator as described herein and a vehicle acceptable for contact with ocular tissue. The vehicle may be aqueous or nonaqueous. The vehicle used in the topical composition may be in the form of a gel, an ointment, a liquid, a cream, or an emulsion. If the vehicle is an emulsion, the emulsion may have a continuous aqueous phase and a discontinuous nonaqueous or oil phase (oil-in-water emulsion), or a continuous nonaqueous or oil phase and a discontinuous aqueous phase (water-in-oil emulsion). When administered topically in liquid or gel form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain coloring and scenting agents.

In certain embodiments, a silicone elastomer (e.g., dimethicone crosspolymer) is employed to increase delivery and penetration of the vasodilator into the ocular tissue.

The pharmaceutical excipients used in the topical preparations of the vasodilator compositions may be selected from the group consisting of solvents, emollients and/or emulsifiers, oil bases, preservatives, antioxidants, tonicity adjusters, penetration enhancers and solubilizers, chelating agents, buffering agents, surfactants, one or more polymers, and combinations thereof.

Suitable solvents for an aqueous or hydrophilic topical formulation include water; ethyl alcohol; isopropyl alcohol; mixtures of water and ethyl and/or isopropyl alcohols; glycerin; ethylene, propylene or butylene glycols; DMSO; and mixtures thereof. Suitable solvents for hydrophobic topical formulations include mineral oils, vegetable oils, and silicone oils. If desired, the vasodilator compositions as described herein may be dissolved or dispersed in a hydrophobic oil phase, and the oil phase may then be emulsified in an aqueous phase comprising water, alone or in combination with lower alcohols, glycerin, and/or glycols. In certain embodiments water is present, but at amounts below the threshold at which a stinging sensation when applied to damaged skin may result. Osmotic shock or osmotic stress is a sudden change in the solute concentration around a cell, causing a rapid change in the movement of water across its cell membrane. Under conditions of high concentrations of either salts, substrates or any solute in the supernatant, water is drawn out of the cells through osmosis. This also inhibits the transport of substrates and cofactors into the cell thus "shocking" the cell. Alternatively, at low concentrations of solutes, water enters the cell in large amounts, causing it to swell and either burst or undergo apoptosis. Certain of the formulations as described herein can be advantageously employed where it is desirable to minimize osmotic shock.

Viscosity of the compositions can be maintained at the selected level using a pharmaceutically acceptable thickening agent. Suitable viscosity enhancers or thickeners which may be used to prepare a viscous gel or cream with an aqueous base include sodium polyacrylate, xanthan gum, polyvinyl pyrrolidone, acrylic acid polymer, carragenans, hydroxyethyl cellulose, hydroxypropyl cellulose, methyl cellulose, ethyl cellulose, propyl cellulose, hydroxypropyl methyl cellulose, polyethoxylated polyacrylamides, polyethoxylated acrylates, and polyethoxylated alkane thiols. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents, or by employing a base that has an acceptable level of viscosity.

Suitable emollients include hydrocarbon oils and waxes such as mineral oil, petrolatum, paraffin, ceresin, ozokerite, microcrystalline wax, polyethylene, squalene, perhydrosqualene, silicone oils, triglyceride esters, acetoglyceride esters, such as acetylated monoglycerides; ethoxylated glycerides, such as ethoxylated glyceryl monostearate; alkyl esters of fatty acids or dicarboxylic acids.

Suitable silicone oils for use as emollients include dimethyl polysiloxanes, methyl(phenyl) polysiloxanes, and water-soluble and alcohol-soluble silicone glycol copolymers. Suitable triglyceride esters for use as emollients include vegetable and animal fats and oils including castor oil, safflower oil, cotton seed oil, corn oil, olive oil, cod liver oil, almond oil, avocado oil, palm oil, sesame oil, and soybean oil.

Suitable esters of carboxylic acids or diacids for use as emollients include methyl, isopropyl, and butyl esters of fatty acids. Specific examples of alkyl esters including hexyl laurate, isohexyl laurate, iso-hexyl palmitate, isopropyl palmitate, decyl oleate, isodecyl oleate, hexadecyl stearate, decyl stearate, isopropyl isostearate, dilauryl lactate, myristyl lactate, and cetyl lactate; and alkenyl esters of fatty acids such as oleyl myristate, oleyl stearate, and oleyl oleate. Specific examples of alkyl esters of diacids include diisopropyl adipate, diisohexyl adipate, bis(hexyldecyl) adipate, and diisopropyl sebacate.

Other suitable classes of emollients or emulsifiers which may be used in the topical formulations include fatty acids, fatty alcohols, fatty alcohol ethers, ethoxylated fatty alcohols, fatty acid esters of ethoxylated fatty alcohols, and waxes.

Specific examples of fatty acids for use as emollients include pelargonic, lauric, myristic, palmitic, stearic, isostearic, hydroxystearic, oleic, linoleic, ricinoleic, arachidic, behenic, and erucic acids. Specific examples of fatty alcohols for use as emollients include lauryl, myristyl, cetyl, hexadecyl, stearyl, isostearyl, hydroxystearyl, oleyl, ricinoleyl, behenyl, and erucyl alcohols, as well as 2-octyl dodecanol.

Specific examples of waxes suitable for use as emollients include lanolin and derivatives thereof including lanolin oil, lanolin wax, lanolin alcohols, lanolin fatty acids, isopropyl lanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysates of lanolin, hydrogenated lanolin, ethoxylated hydrogenated lanolin, ethoxylated sorbitol lanolin, and liquid and semisolid lanolin. Also usable as waxes include hydrocarbon waxes, ester waxes, and amide waxes. Useful waxes include wax esters such as beeswax, spermaceti, myristyl myristate and stearyl stearate; beeswax derivatives, e.g., polyoxyethylene sorbitol beeswax; and vegetable waxes including carnauba and candelilla waxes.

Polyhydric alcohols and polyether derivatives may be used as solvents and/or surfactants in the topical formulations. Suitable polyhydric alcohols and polyethers include propylene glycol, dipropylene glycol, polypropylene glycols 2000 and 4000, poly(oxyethylene-co-oxypropylene) glycols, glycerol, sorbitol, ethoxylated sorbitol, hydroxypropylsorbitol, polyethylene glycols 200-6000, methoxy polyethylene glycols 350, 550, 750, 2000 and 5000, poly[ethylene oxide] homopolymers (100,000-5,000,000), polyalkylene glycols and derivatives, hexylene glycol, 2-methyl-2,4-pentanediol, 1,3-butylene glycol, 1,2,6-hexanetriol, 2-ethyl-1, 3-hexanediol, vicinal glycols having 15 to 18 carbon atoms, and polyoxypropylene derivatives of trimethylolpropane.

Polyhydric alcohol esters may be used as emulsifiers or emollients. Suitable polyhydric alcohol esters include ethylene glycol mono- and di-fatty acid esters, diethylene glycol mono- and di-fatty acid esters, polyethylene glycol (200-6000) mono- and di-fatty acid esters, propylene glycol mono- and di-fatty esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Suitable emulsifiers for use in topical formulations include anionic, cationic, nonionic, and zwitterionic surfactants. Preferred ionic emulsifiers include phospholipids, such as lecithin and derivatives.

Lecithin and other phospholipids may be used to prepare liposomes containing the vasodilators as described herein. Formation of lipid vesicles occurs when phospholipids such as lecithin are placed in water and consequently form one bilayer or a series of bilayers, each separated by water molecules, once enough energy is supplied. Liposomes can be created by sonicating phospholipids in water. Low shear rates create multilamellar liposomes. Continued high-shear sonication tends to form smaller unilamellar liposomes. Hydrophobic chemicals can be dissolved into the phospholipid bilayer membrane. The lipid bilayers of the liposomes deliver the vasodilators as described herein.

The topical formulation may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting formulation contains micelles, i.e., spherical oil droplets surrounded by a membrane of polar surfactant molecules, dispersed in the aqueous solvent.

Sterols including, for example, cholesterol and cholesterol fatty acid esters; amides such as fatty acid amides, ethoxylated fatty acid amides, and fatty acid alkanolamides may also be used as emollients and/or penetration enhancers.

A pharmaceutically acceptable preservative can be employed to increase the shelf life of the composition. Other suitable preservatives and/or antioxidants for use in topical formulations include benzalkonium chloride, benzyl alcohol, phenol, urea, parabens, butylated hydroxytoluene (BHT), butylated hydroxyanisole (BHA), tocopherol, thimerosal, chlorobutanol, or the like, and mixtures thereof, can be employed. If a preservative, such as an antioxidant, is employed, the concentration is typically from about 0.02% to about 2% based on the total weight of the composition, although larger or smaller amounts can be desirable depending upon the agent selected. Reducing agents, as described herein, can be advantageously used to maintain good shelf life of the formulation. It is generally observed that the anhydrous formulations of the embodiments exhibit satisfactory stability, such that a preservative can be omitted from the formulation.

Suitable chelating agents for use in topical formulations include ethylene diamine tetraacetic acid, alkali metal salts thereof alkaline earth metal salts thereof, ammonium salts thereof, and tetraalkyl ammonium salts thereof.

The carrier preferably has a pH of between about 4.0 and 10.0, more preferably between about 6.8 and about 7.8. The pH may be controlled using buffer solutions or other pH modifying agents. Suitable pH modifying agents include phosphoric acid and/or phosphate salts, citric acid and/or citrate salts, hydroxide salts (i.e., calcium hydroxide, sodium hydroxide, potassium hydroxide) and amines, such as triethanolamine. Suitable buffer solutions include a buffer comprising a solution of monopotassium phosphate and dipotassium phosphate, maintaining a pH of between 5.8 and 8; and a buffer comprising a solution of monosodium phosphate and disodium phosphate, maintaining a pH of between 6 and 7.5. Other buffers include citric acid/sodium citrate, and dibasic sodium phosphate/citric acid. The vasodilator compositions of the embodiments are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. It can be desirable to include a reducing agent in the formulation, such as vitamin C, vitamin E, or other reducing agents as are known in the pharmaceutical arts.

Surfactants can also be employed as excipients, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

When the vasodilator formulations of the embodiments are administered by intraocular injection, it is preferably in the form of a pyrogen-free, parenterally acceptable aqueous solution or oleaginous suspension, emulsion or solution. Suspensions can be formulated according to methods well known in the art using suitable dispersing or wetting agents and suspending agents. The preparation of acceptable aqueous or nonaqueous solutions with suitable properties, e.g., pH, isotonicity, stability, and the like, is within the skill in the art. For example, an isotonic vehicle such as 1,3-butanediol, water, isotonic sodium chloride solution, Ringer's solution, dextrose solution, dextrose and sodium chloride solution, lactated Ringer's solution, or other vehicles as are known in the art can be employed, or a fixed oil can be employed conventionally as a solvent or suspending medium, e.g., synthetic mono or diglycerides, fatty acids, or the like. The vasodilator formulations can also contain stabilizers, preservatives, buffers, antioxidants, or other additives known to those of skill in the art.

In certain embodiments, it can be advantageous to include additional agents having pharmacological activity. Anti-infective agents include, but are not limited to, anthelmintic (mebendazole), antibiotics including aminoglycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin, clindamycin, colistimethate sodium, polymyxin b sulfate, vancomycin, antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine, quinolones (ciprofloxacin, levofloxacin), sulfonamides (sulfadiazine, sulfisoxazole), sulfones (dapsone), furazolidone, metronidazole, pentamidine, sulfanilamidum crystallinum, gatifloxacin, and sulfamethoxazole/trimethoprim. Anesthetics can include, but are not limited to, ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and phenazopyridine. Anti-inflammatory agents include but are not limited to, nonsteroidal anti-inflammatory drugs (NSAIDs) such as aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinonide, betamethasone dipropionate, betamethasone valerate, desonide, desoximetasone, fluocinolone, triamcinolone, clobetasol propionate, and dexamethasone.

Kits for Administration of Compositions

Some embodiments of the methods and compositions provided herein include kits comprising vasodilators provided herein. In some embodiments, kits can be provided to an administering physician, other health care professional, a patient, or a caregiver. In some embodiments, a kit comprises a container which contains the vasodilator(s) in a suitable topical formulation, and instructions for administering the composition to a subject. The kit can optionally also contain one or more additional therapeutic or other agents. For example, a kit containing a vasodilator blocker in topical form can be provided along with other agents such as topical antibiotics or topical anesthetics. The kit may contain the vasodilator in bulk form, or can contain separate doses of the vasodilator for serial or sequential administration. The kit can optionally contain one or more diagnostic tools, administration tools, and/or instructions for use, e.g., syringes for intraocular injection. The kit can contain suitable delivery devices, such as, syringes, pump dispensers, wands, single dose packets, and the like, along with instructions for administering the vasodilator compositions and any other therapeutic or beneficial agents. The kit can optionally contain instructions for storage, reconstitution (if applicable), and administration of any or all therapeutic or beneficial agents included. The kits can include a plurality of containers reflecting the number of administrations to be given to a subject, or the different products to be administered to the subject.

The topical formulation for administration to tissue of the eye, in addition to the vasodilator, can contain other ingredients.

While topical administration of the vasodilator disclosed herein can advantageously be employed, in certain embodiments other routes of administration are also contemplated, such as intraocular injection.

The vasodilator compositions described herein can be administered by themselves to a subject, or in compositions where they are mixed with other active agents, as in combination therapy, or with carriers, diluents, excipients or combinations thereof. Formulation is dependent upon the route of administration chosen. Techniques for formulation and administration of the compounds described herein are known to those skilled in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

The vasodilator compositions disclosed herein may be manufactured into administrable forms by a process that is itself known, e.g., by means of conventional mixing, dissolving, granulating, dragee-making, levigating, emulsifying, encapsulating, entrapping, tableting, or extracting processes.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Contemplated herein is any combination of the forgoing, or other methods as would be known to one of ordinary skill in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

In practice, the vasodilator may be combined as the active ingredient in intimate admixture with a pharmaceutical carrier according to conventional pharmaceutical compounding techniques. The excipients are preferably minimized so as to ensure administration of an appropriate amount of vasodilator in a compact format. The carrier can take a wide variety of forms depending on the form of preparation desired for administration. Thus, the vasodilator compositions provided herein can be presented as discrete units suitable for administration each containing a predetermined amount of the active ingredient. Further, the vasodilator compositions can be presented as an oil, as a solution, as a suspension in an aqueous liquid, as a non-aqueous liquid, as an oil-in-water emulsion, or as a water-in-oil liquid emulsion, similar to the topical formulations described elsewhere herein, but using components suitable for human contact or consumption. In addition to the common dosage forms set out above, the vasodilator compositions provided herein can also be administered by controlled release and/or delivery devices. The vasodilator compositions can be prepared by any of the methods of pharmacy. In general, such methods include a step of bringing into association the active ingredient with the carrier that constitutes one or more necessary ingredients. In general, the vasodilator compositions are prepared by uniformly and intimately admixing the vasodilator ingredient(s) with liquid carriers or finely divided solid carriers or both. The product can then be conveniently shaped into the desired presentation.

A vasodilator formulation may also be administered in a local manner, for example, via injection of the vasodilator composition directly into a target area, e.g., in a depot or sustained release formulation intraocularly. Furthermore, a targeted drug delivery system for the vasodilator may be used, for example, in a liposome coated with a tissue specific antibody.

The vasodilator compositions may contain the vasodilator in an amount effective for the desired therapeutic effect. In some embodiments, the vasodilator compositions are in a unit dosage form and comprise from about 0.1 mg or less to about 5000 mg or more of vasodilator per unit dosage form. In further embodiments, the vasodilator compositions comprise from about 1 to about 500 mg per unit dosage form or from about 500 to 5000 mg per unit dosage form of vasodilator. Such amounts can be selected depending upon the vasodilator employed. Such dosage forms may be solid, semisolid, liquid, an emulsion, or adapted for delivery via aerosol or the like.

The carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, lower alcohols, and water. Examples of gaseous carriers include carbon dioxide and nitrogen.

Vasodilator compositions provided herein can be prepared as solutions or suspensions of the vasodilator in water or nonaqueous liquids. A suitable surfactant can be included such as, for example, hydroxypropylcellulose. Dispersions can also be prepared in glycerol, liquid polyethylene glycols, and mixtures thereof in oils. Further, a preservative can be included to, for example, prevent the detrimental growth of microorganisms.

Vasodilator compositions provided herein suitable for injectable use include sterile aqueous solutions or dispersions. Furthermore, the vasodilator compositions can be in the form of sterile powders for the extemporaneous preparation of such sterile injectable solutions or dispersions. The vasodilator compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

In addition to the aforementioned carrier ingredients, the vasodilator formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood or other bodily fluids of the intended recipient. Vasodilator compositions can also be prepared in powder or liquid concentrate form for dilution.

Contemplated herein are vasodilator compositions including one or more vasodilators as described herein in combination with at least one additional active agent, e.g., an antibiotic. The vasodilator and the at least one additional active agent(s) may be present in a single formulation or in multiple formulations provided together, or may be unformulated. In some embodiments, the vasodilator can be administered with one or more additional agents together in a single composition. For example, the vasodilator can be administered in one composition, and at least one of the additional agents can be administered in a second composition. In a further embodiment, the vasodilator and the at least one additional active agent(s) are co-packaged in a kit. For example, a drug manufacturer, a drug reseller, a physician, a compounding shop, or a pharmacist can provide a kit comprising the vasodilator in combination with another product or component for delivery to a patient. Such additional components can include anti-infective agents, anti-inflammatory agents, anesthetics, or the like.

Some embodiments described herein relate to compositions of vasodilator, which can include a therapeutically effective amount of the vasodilator described herein and a pharmaceutically acceptable carrier, diluent, excipient or combination thereof. The vasodilator composition can include the vasodilator in an amount for example, >1%, ≥2%, ≥3%, ≥4%, ≥5%, ≥6%, ≥7%, ≥8%, ≥9%, ≥10%, ≥20%, ≥30%, ≥40%, ≥50%, ≥60%, ≥70%, ≥80%, ≥90%, ≥95%, or ≥98% of the composition.

EXAMPLES

Example 1

A patient is diagnosed with wet macular degeneration. A composition comprising the calcium channel blocker nifedipine is directly applied to the vitreous surface of one eye while the other eye is left untreated. The treated eye is observed to have reduced symptoms of wet macular degeneration than the untreated eye.

Example 2

A patient is diagnosed with wet macular degeneration. A composition comprising the ACE inhibitor enalapril is directly applied to the vitreous surface of one eye while the other eye is left untreated. The treated eye is observed to have reduced symptoms of wet macular degeneration than the untreated eye.

Example 3

A patient is diagnosed with wet macular degeneration. A composition comprising the angiotensin receptor blocker losartan is directly applied to the vitreous surface of one eye while the other eye is left untreated. The treated eye is observed to have reduced symptoms of wet macular degeneration than the untreated eye.

Example 4

A patient is diagnosed with dry macular degeneration. A composition comprising the calcium channel blocker nifedipine is directly applied to the vitreous surface of one eye while the other eye is left untreated. The treated eye is observed to have reduced symptoms of dry macular degeneration than the untreated eye.

Example 5

A patient is diagnosed with dry macular degeneration. A composition comprising the ACE inhibitor enalapril is directly applied to the vitreous surface of one eye while the other eye is left untreated. The treated eye is observed to have reduced symptoms of dry macular degeneration than the untreated eye.

Example 6

A patient is diagnosed with dry macular degeneration. A composition comprising the angiotensin receptor blocker losartan is directly applied to the vitreous surface of one eye while the other eye is left untreated. The treated eye is observed to have reduced symptoms of dry macular degeneration than the untreated eye.

Example 7

A patient is diagnosed with wet macular degeneration. A composition comprising the calcium channel blocker nifedipine is directly injected into the intraocular space of one eye while the other eye is left untreated. The treated eye is observed to have reduced symptoms of wet macular degeneration than the untreated eye.

Example 8

A patient is diagnosed with wet macular degeneration. A composition comprising the ACE inhibitor enalapril is directly injected into the intraocular space of one eye while the other eye is left untreated. The treated eye is observed to have reduced symptoms of wet macular degeneration than the untreated eye.

Example 9

A patient is diagnosed with wet macular degeneration. A composition comprising the angiotensin receptor blocker losartan is directly injected into the intraocular space of one eye while the other eye is left untreated. The treated eye is observed to have reduced symptoms of wet macular degeneration than the untreated eye.

Example 10

A patient is diagnosed with dry macular degeneration. A composition comprising the calcium channel blocker nifedipine is directly injected into the intraocular space of one eye while the other eye is left untreated. The treated eye is observed to have reduced symptoms of dry macular degeneration than the untreated eye.

Example 11

A patient is diagnosed with dry macular degeneration. A composition comprising the ACE inhibitor enalapril is directly injected into the intraocular space of one eye while the other eye is left untreated. The treated eye is observed to have reduced symptoms of dry macular degeneration than the untreated eye.

Example 12

A patient is diagnosed with dry macular degeneration. A composition comprising the angiotensin receptor blocker losartan is directly injected into the intraocular space of one eye while the other eye is left untreated. The treated eye is observed to have reduced symptoms of dry macular degeneration than the untreated eye.

Exemplary Pharmaceutical Compositions and Methods

Pharmaceutical Composition 1: A pharmaceutical composition for the treatment or prophylaxis of macular degeneration, comprising: at least one vasodilator; and at least one pharmaceutical excipient.

Pharmaceutical Composition 2: Pharmaceutical Composition 1, for the treatment or prophylaxis of wet macular degeneration.

Pharmaceutical Composition 3: Pharmaceutical Composition 1, for the treatment or prophylaxis of dry macular degeneration.

Pharmaceutical Composition 4: Any One of Pharmaceutical Compositions 1 through 3, in a form adapted for direct administration or intraocular injection to the eye.

Pharmaceutical Composition 5: Pharmaceutical Composition 4, wherein the form is selected from the group consisting of an oil, a liquid and a suspension for direct application on the vitreous surface of the eye.

Pharmaceutical Composition 6: Any One of Pharmaceutical Compositions 1 through 3, formulated as a liquid or a suspension of the at least one vasodilator, wherein the vasodilator is a contact vasodilator.

Pharmaceutical Composition 7: Any One of Pharmaceutical Compositions 1 through 6, wherein the vasodilator is a calcium channel blocker.

Pharmaceutical Composition 8: Pharmaceutical Composition 7, wherein the at least one calcium channel blocker is a dihydropyridine selected from the group consisting of nifedipine, isradipine, felodipine, amlodipine, nicardipine, and clevidipine.

Pharmaceutical Composition 9: Pharmaceutical Composition 7, wherein the at least one calcium channel blocker is a non dihydropyridine selected from the group consisting of verapamil and diltiazem.

Pharmaceutical Composition 10: Any One of Pharmaceutical Compositions 1 through 6, wherein the vasodilator is an ACE inhibitor.

Pharmaceutical Composition 11: Pharmaceutical Composition 10, wherein the ACE inhibitor is selected from the group consisting of benazepril, captopril, enalapril, fosinopril, lisinopril, moexipril, perindopril, quinapril, ramipril, and trandolapril.

Pharmaceutical Composition 12: Any One of Pharmaceutical Compositions 1 through 6, wherein the vasodilator is an angiotensin receptor blocker.

Pharmaceutical Composition 13: Pharmaceutical Composition 12, wherein the angiotensin receptor blocker is selected from the group consisting of azilsartan, candesartan, eprosartan, irbesartan, losartan, olmesartan, telmisartan, and valsartan Pharmaceutical Composition 14: Any One of Pharmaceutical Compositions 1 through 6, wherein the vasodilator is a nitrate.

Pharmaceutical Composition 15: Pharmaceutical Composition 14, wherein the nitrate is selected from the group consisting of nitroglycerin, isosorbide mononitrate and isosorbide dinitrate.

Pharmaceutical Composition 16: Any One of Pharmaceutical Compositions 1 through 6, wherein the vasodilator is an alpha blocker.

Pharmaceutical Composition 17: Pharmaceutical Composition 16, wherein the alpha blocker is selected from the group consisting of doxazosin, prazosin, and terazosin.

Pharmaceutical Composition 18: Any One of Pharmaceutical Compositions 1 through 6, wherein the vasodilator is a beta blocker.

Pharmaceutical Composition 19: Pharmaceutical Composition 18, wherein the beta blocker is selected from the group consisting of acebutolol, atenolol, bisoprolol fumarate, carvedilol, esmilol, labetalol, metoprolol tartrate, metoprolol succinate, nadolol, nebivolol, penbutolol sulfate, propranolol, sotalol, hydrochlorothiazide, and bisoprolol.

Pharmaceutical Composition 20: Any One of Pharmaceutical Compositions 1 through 6, wherein the vasodilator is hydralazine.

Pharmaceutical Composition 21: Any One of Pharmaceutical Compositions 1 through 6, wherein the vasodilator is an angiotensin receptor-neprilysin inhibitor.

Pharmaceutical Composition 22: Pharmaceutical Composition 21, wherein the angiotensin receptor-neprilysin inhibitor is sacubitril/valsartan.

Pharmaceutical Composition 23: Any One of Pharmaceutical Compositions 1 through 22, wherein the concentration of the vasodilator is about 0.0001 mg per ml to 1000 mg per ml, optionally 1 mg per ml to 10 mg per ml, optionally 1 mg per ml to 1000 mg per ml, optionally 5 mg per ml to 10 mg per ml, optionally 10 mg per ml, optionally 20 mg per ml, optionally 30 mg per ml, optionally 60 mg per ml, optionally 90 mg per ml, optionally 120 mg per ml, optionally 180 mg per ml, optionally 240 mg per ml.

Pharmaceutical Composition 24: Any One of Pharmaceutical Compositions 1 through 2, wherein the concentration of the vasodilator is from about 0.0001% by weight to about 20% by weight, optionally about 0.01% by weight, optionally about 0.1% by weight, optionally about 1% by weight, optionally about 10% by weight, optionally about 20% by weight.

Method 25: A method for the treatment or prophylaxis of macular degeneration in a patient in need thereof, comprising: administering an effective amount of the pharmaceutical composition according to any one of Pharmaceutical Compositions 1 through 24 to a patient in need thereof.

Method 26: Method 25, for the treatment or prophylaxis of wet macular degeneration.

Method 27: Method 25, for the treatment or prophylaxis of dry macular degeneration.

Method 28: Method 25, wherein the composition is administered once a day, optionally two or more times a day, optionally once a week, optionally two or more times a week, optionally once a month, optionally two or more times a month, optionally a plurality of times a year.

Any of the features the above referenced pharmaceutical compositions, uses, and methods is applicable to any other pharmaceutical composition, use, or method identified herein. Moreover, any of the features of the above referenced pharmaceutical compositions, uses, and methods is independently combinable, partly or wholly, with other embodiments of the pharmaceutical compositions, uses, and methods described herein in any way, e.g., one, two, or three or more features may be combinable in whole or in part. Further, any of the features of the pharmaceutical compositions, uses, and methods described above may be made optional to other pharmaceutical compositions, uses, and methods described herein. Any aspect or embodiment of a method or use described herein can be performed using a composition, e.g., a pharmaceutical composition and/or a compound as described herein, and any aspect or embodiment of a composition, e.g., a pharmaceutical composition and/or a compound described herein, can be used or adapted to perform a method or use as described herein.

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and "one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for the treatment of macular degeneration in a patient in need thereof, comprising:
    topically administering an effective amount of a pharmaceutical composition comprising:
    at least one vasodilator; and
    at least one pharmaceutical excipient to a patient in need thereof.

2. The method of claim 1, for the treatment of wet macular degeneration.

3. The method of claim 1, for the treatment of dry macular degeneration.

4. The method of claim 1, wherein the composition is administered once a day, optionally two or more times a day, optionally once a week, optionally two or more times a week, optionally once a month, optionally two or more times a month, optionally a plurality of times a year.

5. The method of claim 1, wherein the composition comprises gels, drops, sprays, liquids, ointments, creams, emulsions or aerosols.

6. The method of claim 1, wherein the at least one vasodilator is an ACE inhibitor.

7. The method of claim 1, wherein the composition further comprises a carrier selected from cyclosiloxane or linear silicone.

8. The method of claim 7, wherein the carrier comprises 80 wt % to 95 wt % of the composition.

9. The method of claim 1, wherein the composition further comprises one or more of a diluent, an excipient, a wetting or emulsifying agent, a pH buffering agent, a gelling or viscosity enhancing additive, a preservative, a scenting agent, or a coloring agent.

10. The method of claim 5, wherein the emulsion comprises a continuous aqueous phase and a discontinuous oil phase or a continuous oil phase and a discontinuous aqueous phase.

11. The method of claim 1, wherein the at least one vasodilator is a calcium channel blocker.

12. The method claim 11, wherein the calcium channel blocker is nifedipine.

* * * * *